US011441127B2

United States Patent
Jordan et al.

(10) Patent No.: US 11,441,127 B2
(45) Date of Patent: Sep. 13, 2022

(54) LIVE ATTENUATED ARKANSAS SEROTYPE INFECTIOUS BRONCHITIS VIRUS VACCINE

(71) Applicant: UNIVERSITY OF GEORGIA RESEARCH FOUNDATION, INC., Athens, GA (US)

(72) Inventors: Brian J. Jordan, Watkinsville, GA (US); Mark W. Jackwood, Watkinsville, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 7 days.

(21) Appl. No.: 17/132,182

(22) Filed: Dec. 23, 2020

(65) Prior Publication Data

US 2021/0115410 A1    Apr. 22, 2021

Related U.S. Application Data

(60) Continuation of application No. 16/410,340, filed on May 13, 2019, now abandoned, which is a division of application No. 15/880,972, filed on Jan. 26, 2018, now Pat. No. 10,329,538.

(60) Provisional application No. 62/583,270, filed on Nov. 8, 2017, provisional application No. 62/451,335, filed on Jan. 27, 2017.

(51) Int. Cl.
| | |
|---|---|
| *C12N 7/00* | (2006.01) |
| *A61K 39/215* | (2006.01) |
| *C07K 14/005* | (2006.01) |
| *A61K 39/12* | (2006.01) |
| *A61P 31/14* | (2006.01) |
| *A61K 39/00* | (2006.01) |

(52) U.S. Cl.
CPC ............... *C12N 7/00* (2013.01); *A61K 39/12* (2013.01); *A61K 39/215* (2013.01); *A61P 31/14* (2018.01); *C07K 14/005* (2013.01); *A61K 2039/5254* (2013.01); *A61K 2039/542* (2013.01); *A61K 2039/543* (2013.01); *A61K 2039/552* (2013.01); *C12N 2770/20021* (2013.01); *C12N 2770/20022* (2013.01); *C12N 2770/20034* (2013.01); *C12N 2770/20064* (2013.01); *C12N 2770/20071* (2013.01)

(58) Field of Classification Search
CPC ...... A61K 2039/552; A61K 2039/5254; A61K 39/12; A61K 39/215; A61K 2039/543; A61K 2039/545; A61K 2039/525; A61K 2039/54; A61K 2039/541; A61K 39/00; A61K 2039/542; A61K 2039/70; C07K 14/005; C07K 14/165; C07K 2319/735; C12N 2770/20034; C12N 2770/20022; C12N 7/00; C12N 2770/20064; C12N 2770/20021; C12N 2770/20071; C12N 2770/20061; C12N 15/86; C12N 2770/20051; C12N 2770/20062

See application file for complete search history.

(56) References Cited

U.S. PATENT DOCUMENTS

| | | |
|---|---|---|
| 6,214,538 B1 | 4/2001 | Jackwood et al. |
| 8,679,504 B2 | 3/2014 | Sellers et al. |
| 9,790,474 B2 | 10/2017 | Sellers |
| 2011/0268762 A1 | 11/2011 | Toro et al. |
| 2014/0127264 A1 | 5/2014 | Verheije et al. |
| 2017/0360540 A1 | 12/2017 | Jackwood et al. |
| 2018/0216082 A1 | 8/2018 | Jordan et al. |

FOREIGN PATENT DOCUMENTS

| | | |
|---|---|---|
| WO | WO 2009/143332 A2 | 11/2009 |
| WO | WO 2014/078561 A1 | 5/2014 |
| WO | WO 2016/064841 A1 | 4/2016 |
| WO | WO 2018/140714 A1 | 8/2018 |

OTHER PUBLICATIONS

International Patent Application No. PCT/US2018/015427, filed Jan. 26, 2018; International Search Report and Written Opinion dated May 31, 2018; 10 pages.

National Center for Biotechnology Information, National Library of Medicine, National Institutes of Health, GenBank Locus IBBSPIKE, Accession No. L10384, "Infectious bronchitis virus spike protein, complete cds.," [online], Bethesda, MD [retrieved on Dec. 26, 2018], Retrieved from the Internet: <URL:ncbi.nlm.nih.gov/nuccore/L10384.1/>; 2 pgs.

National Center for Biotechnology Information, National Library of Medicine, National Institutes of Health, GenBank Locus GQ504721, Accession No. GQ504721, "Infectious bronchitis virus strain Arkansas Vaccine, complete genome" [online], Bethesda, MD [retrieved on Oct. 31, 2018], Retrieved from the Internet: <URL:ncbi.nlm.nih.gov/nucleotide/394397114?report=genbank&log$=nuclalign&blast_rank=1&RID=8DBVN1E0015>; 11 pgs.

Albanese et al., Abstract T141 "Development of a potential IBV Arkansas serotype vaccine candidate: Arkansas GA" 2017 International Poultry Scientific Forum, Southern Conference on Avian Diseases (SCAD) Meeting, Atlanta GA, Jan. 31, 2017; Abstract T141, p. 287. Retrieved from the Internet: <https://www.poultryscience.org/psa17/abstracts/286.pdf> on Dec. 13, 2018. 1 page.

(Continued)

*Primary Examiner* — Rachel B Gill
(74) *Attorney, Agent, or Firm* — Mueting Raasch Group

(57) ABSTRACT

Attenuated isolates of the Arkansas serotype of infectious bronchitis virus (IBV), including the IBV isolate ArkGA p40 deposited at the ATCC under Patent Designation PTA-126834, and compositions thereof are presented. Methods for administering the isolates or compositions as vaccines to the prevent virulent IBV infection in birds of the order Galliformes are also presented.

16 Claims, 11 Drawing Sheets

Specification includes a Sequence Listing.

(56) References Cited

OTHER PUBLICATIONS

Albanese et al., AbstractT139 "Attenuation characteristics of ArkGA, a new Ark-type IBV vaccine candidate" 2018 International Poultry Scientific Forum, Jan. 29, 2018; Abstract T139, p. 41. Retrieved from the Internet: <poultryscience.org/spss2018/2018_SPSS_Abstracts.pdf> on Apr. 8, 2018. 1 page.

Albanese et al., "Biological and molecular characterization of ArkGA: A novel Arkansas serotype vaccine that is highly attenuated, efficacious, and protective against homologous challenge" Vaccine, Oct. 1, 2018; 36(41):6077-86. Epub Sep. 7, 2018.

Albanese et al., Spike protein [Infectious bronchitis virus], Gen Bank: AYA44721.1. Dep. Sep. 24, 2018.

Albanese et al., Infectious bronchitis virus isolate ArkGA_P60, complete genome. GenBank: MH779859.1. Dep. Sep. 24, 2018.

Albanese Examination and Comparison of Infectious Bronchitis Virus and Coccidia Vaccines and Vaccination Methods, 2017, 12, PhD Dissertation, University of Georgia.

Alvarado et al., "Detection of Massachusetts and Arkansas Serotypes of Infectious Bronchitis Virus in Broilers" *Avian Dis*, Jun. 2006; 50(2):292-7.

Ammayappan et al., "Complete genomic sequence analysis of infectious bronchitis virus Ark DPI strain and its evolution by recombination" *Virol J*, 2008; 5:157. 7 pages.

Ammayappan et al., "Identification of sequence changes responsible for the attenuation of avian infectious bronchitis virus strain Arkansas DPI," *Arch Virol*, 2009; 154(3):495-9. Epub Feb. 14, 2009.

Armesto et al., "A recombinant avian infectious bronchitis virus expressing a heterologous spike gene belonging to the 4/91 serotype" *PLoS One*, 2011; 6(8):e24352. Epub Aug. 30, 2011.

Ashby et al., "Evaluating the pathogenicity of the infectious bronchitis virus Arkansas 99 vaccine," 2015 International Poultry Scientific Forum [online]. Poster Abstract No. P220, Atlanta GA, Jan. 27, 2015, available online [retrieved on Dec. 14, 2018], Retrieved from the Internet: <URL:poultryscience.org/psa15/abstracts/252.pdf>; p. 254. 1 page.

Bande et al., "Progress and challenges toward the development of vaccines against avian infectious bronchitis" *J Immunol Res*, 2015; 2015:424860. Epub Apr. 14, 2015. 12 pages.

Bentley et al., "Infectious bronchitis virus as a vector for the expression of heterologous genes" *PLoS One*, Jun. 26, 2013; 8(6):e67875. Print 2013.

Britton et al., "Generation of a recombinant avian coronavirus infectious bronchitis virus using transient dominant selection" *J Virol Methods*, Feb. 2005, 123(2):203-11.

Bru et al., "Protection of chickens vaccinated with combinations of commercial live infectious bronchitis vaccines containing Massachusetts, Dutch and QX-like serotypes against challenge with virulent infectious bronchitis viruses 793B and IS/1494/06 Israel variant 2" *Avian Pathol*, Feb. 2017; 46(1):52-8, Epub Oct. 17, 2016.

Callison et al., "Rapid Differentiation of avian infectious bronchitis virus isolates by sample to residual ratio quantitation using real-time reverse transcriptase-polymerase chain reaction" *J Virol Methods*, 2005; 124:183-90.

Callison et al., "Development and evaluation of a real-time Taqman RT-PCR assay for the detection of infectious bronchitis virus from infected chickens " *J Virol*, Methods, 2006; 138:60-5.

Casais et al., "Reverse genetics system for the avian coronavirus infectious bronchitis virus" *J Virol*, Dec. 2001; 75(24):12359-69.

Casais et al., "Recombinant avian infectious bronchitis virus expressing a heterologous spike gene demonstrates that the spike protein is a determinant of cell tropism" *J Virol*, Aug. 2003; 77(16):9084-9.

Casais et al., "Gene 5 of the avian coronavirus infectious bronchitis virus is not essential for replication" *J Virol*, Jul. 2005; 79(13):8065-78.

Cavanagh et al., "Amino acids within hypervariable region 1 of avian coronavirus IBV (Massachusetts serotype) spike glycoprotein are associated with neutralization epitopes" *Virus Res*, Sep. 1988; 11(2):141-50.

Cavanagh, "A nomenclature for avian coronavirus isolates and the question of species status" *Avian Pathol*, Apr. 2001; 30(2):109-15.

Cavanagh, "Severe acute respiratory syndrome vaccine development: experiences of vaccination against avian infectious bronchitis coronavirus" *Avian Pathol*; Dec. 2003; 32(6):567-82.

Cavanagh, "Coronaviruses in poultry and other birds" *Avian Pathol*, Dec. 2005; 34(6):439-48.

Cavanagh, "Coronavirus avian infectious bronchitis virus" *Vet Res*, Mar.-Apr. 2007; 38(2):281-97, Epub Feb. 13, 2007.

Cavanagh et al., "Manipulation of the infectious bronchitis coronavirus genome for vaccine development and analysis of the accessory proteins" *Vaccine*, Jul. 26, 2007; 25(30):5558-62. Epub Mar. 6, 2007.

Cook et al., "The use of chicken tracheal organ cultures for the isolation and assay of avian infectious bronchitis virus" *Arch Virol*, 1976; 50(1-2):109-18.

Cook et al., "Breadth of protection of the respiratory tract provided by different live-attenuated infectious bronchitis vaccines against challenge with infectious bronchitis viruses of heterologous serotypes" *Avian Pathol*, Oct. 1999; 28(5):477-85.

Darteil et al., "Herpesvirus of turkey recombinant viruses expressing infectious bursal disease virus (IBDV) VP2 immunogen induce protection against an IBDV virulent challenge in chickens" *Virology*, Aug. 20, 1995; 211(2):481-90.

De Wit et al., "Increased level of protection of respiratory tract and kidney by combining different infectious bronchitis virus vaccines against challenge with nephropathogenic Brazilian genotype sub-cluster 4 strains" *Avian Pathol*, Oct. 2015; 44(5):352-7.

De Wit et al., "Factors influencing the outcome of infectious bronchitis vaccination and challenge experiments" *Avian Pathol*, 2014; 43(6):485-97.

Dufour-Zavala, *A Laboratory Manual for the Isolation, Identification and Characterization of Avian Pathogens*, American Association of Avian Pathologists: Jacksonville, FL; 2008. 5$^{th}$ edition. Cover page, title page and table of contents.

Falchieri et al., "Avian metapneumoviruses expressing Infectious Bronchitis virus genes are stable and induce protection" *Vaccine*, May 24, 2013; 31(22):2565-71. Epub Apr. 12, 2013.

Fields, "Arkansas 99, a New Infectious Bronchitis Serotype," *Avian Diseases*, Jul.-Sep. 1973; 17(3):659-61.

Gelb et al., "Protection afforded infectious bronchitis virus-vaccinated sentinel chickens raised in a commercial environment" *Avian Dis*, Oct.-Dec. 1989; 33(4):764-9.

Guo et al., "Priming with a DNA vaccine and boosting with an inactivated vaccine enhance the immune response against infectious bronchitis virus" *J Virol Methods*, Jul. 2010; 167(1):84-9. Epub Mar. 20, 2010.

Hanada et al., "A large variation in the rates of synonymous substitution for RNA viruses and its relationship to a diversity of viral infection and transmission modes" *Mol Biol Evol*, Jun. 2004; 21(6):1074-80, with Publisher's Correction to Table 2.

Hodgson et al., "Recombinant infectious bronchitis coronavirus Beaudette with the spike protein gene of the pathogenic M41 strain remains attenuated but induces protective immunity" *J Virol*, Dec. 2004; 78(24):13804-11.

International Patent Application No. PCT/US2018/015427, filed Jan. 26, 2018; International Preliminary Report on Patentability dated Aug. 8, 2019; 6 pages.

Jackwood et al., "Further Development and Use of a Molecular Serotype Identification Test for Infectious Bronchitis Virus" *Avian Dis*, Jan.-Mar. 1997; 41(1):105-10.

Jackwood et al., "Data from 11 years of molecular typing infectious bronchitis virus field isolates," *Avian Dis*; Dec. 2005., 49(4):614-618.

Jackwood et al., "Molecular and Serologic Characterization, Pathogenicity, and Protection Studies with Infectious Bronchitis Virus Field Isolates from California" *Avian Diseases*, Jun. 2007; 51(2):527-33.

Jackwood et al., "Infectious bronchitis virus field vaccination coverage and persistence of Arkansas-type viruses in commercial broilers" *Avian Dis*, Jun. 2009; 53(2):175-83.

Jackwood et al., "Rapid heat-treatment attenuation of infectious bronchitis virus" *Avian Pathol*, Jun. 2010; 39(3):227-33.

Jackwood, "Review of infectious bronchitis virus around the world" *Avian Dis*, Dec. 2012; 56(4):634-41.

(56) References Cited

OTHER PUBLICATIONS

Jackwood et al., "Molecular evolution and emergence of avian gammacoronaviruses" *Infect Genet Evol*, Aug. 2012; 12(6):1305-11, Epub May 17, 2012.
Jackwood and de Wit, "Infectious Bronchitis" in *Diseases of Poultry*, Wiley-Blackwell Publishing: Ames, IA. 2013; Cover page, title page, table of contents, and pp. 139-160.
Jackwood et al., "Evaluating Protection Against Infectious Bronchitis Virus by Clinical Signs, Ciliostasis, Challenge Virus Detection, and Histopathology" *Avian Dis*, Sep. 2015; 59(3):368-74.
Jia et al., "A novel variant of avian infectious bronchitis virus resulting from recombination among three different strains" *Arch Virol*, 1995; 140(2):259-71.
Jia et al., "Analysis of the Serotype-Specific Epitopes of Avian Infectious Bronchitis Virus Strains Ark99 and Mass41" *J Virol*, Oct. 1996; 70(10):7255-9.
Johnson et al., "A New Serotype of Infectious Bronchitis Virus Responsible for Respiratory Disease in Arkansas Broiler Flocks" *Avian Dis*, Jul.-Sep. 1973; 17(3):518-23.
Johnson et al., "A recombinant fowl adenovirus expressing the S1 gene of infectious bronchitis virus protects against challenge with infectious bronchitis virus" *Vaccine*, Jun. 20, 2003; 21(21-22):2730-6.
Jordan, "Spray Application of Infectious Bronchitis Virus Vaccines in the Hatchery: How Efficient are We?" The Poultry Informed Professional, Jan./Feb. 2015; Issue 135: pp. 1-4. [retrieved on Dec. 26, 2018] from the Internet. Retrieved from the Internet: <URL: uga.edu/images/uploads/pdrc/PIP_Jan-Feb_15_Final.pdf>; 4 pgs.
Jordan, "Vaccination Against Infectious Bronchitis Virus: A Continuous Challenge" *Vet Microbiol*, Jul. 2017; 206:137-43. Epub Jan. 4, 2017.
Jordan et al., "Molecular Characterization of the ArkGA Infectious Bronchitis Vaccine," American Association of Avian Pathologists (AAAP) Annual Meeting. Powerpoint Presentation Presented on Jul. 23, 2017, Indianapolis, IN, Jul. 21-25, 2017. 24 pages.
Program from the American Association of Avian Pathologists (AAAP) Annual Meeting. Indianapolis, IN, Jul. 21-25, 2017. 24 pages. Jordan et al., Molecular Characterization of the ArkGA Infectious Bronchitis Vaccine on p. 11.
Meeting Summary for the American Association of Avian Pathologists (AAAP) Annual Meeting. Indianapolis, IN, Jul. 21-25, 2017. 1 page. Retrieved online [Aug. 17, 2017] Retrieved on the Internet <URL:aaap.info/2017-annual-meeting-indianapolis>1 page.
Jordan et al., "Molecular Characterization of the ArkGA Infectious Bronchitis Vaccine," American Association of Avian Pathologists (AAAP) Annual Meeting. Poster Presented on Jul. 23, 2017, Indianapolis, IN, Jul. 21-25, 2017. 1 page.
Kant et al., "Location of antigenic sites defined by neutralizing monoclonal antibodies on the S1 avian infectious bronchitis virus glycopolypeptide" *J Gen Virol*, Mar. 1992; 73(Pt 3):591-6.
King and Hopkins, "Evaluation of the hemagglutination-inhibition test for measuring the response of chickens to avian infectious bronchitis virus vaccination" Avian Dis, Jan.-Mar. 1983; 27(1):100-12.
Koch et al., "Antigenic domains on the peplomer protein of avian infectious bronchitis virus: correlation with biological functions" *J Gen Virol*, Sep. 1990; 71(Pt 9):1929-35.
Kusters et al., "Sequence evidence for RNA recombination in field isolates of avian coronavirus infectious bronchitis virus" *Vaccine*, Dec. 1990; 8(6):605-8.
Kwon et al., "Differentiation of infectious bronchitis virus serotypes using polymerase chain reaction and restriction fragment length polymorphism analysis" *Avian Dis*, Jan.-Mar. 1993; 37(1):194-202.
Lashgari and Newman, "Serological comparison and antigenic relationships of seven serotypes of infectious bronchitis virus using the hemagglutination-inhibition test" *Avian Dis*, Apr.-Jun. 1984; 28(2):435-43.

Lashgari and Newman, "Determination of the antigenic relationships within the Massachusetts (M41) type of infectious bronchitis virus using the hemagglutination-inhibition test" *Avian Dis*, Apr.-Jun. 1984; 28(2):444-52.
Lee et al., "Redesign of Primer and Application of the Reverse Transcriptase-Polymerase Chain Reaction and Restriction Fragment Length Polymorphism Test to the DE072 Strain of Infectious Bronchitis Virus," *Avian Dis*, Jul.-Sep. 2000.; 44(3):650-4.
Lee and Jackwood, "Evidence of genetic diversity generated by recombination among avian coronavirus IBV" *Arch Virol*, 2000; 145(10):2135-48.
Lee and Jackwood, "Origin and evolution of Georgia 98 (GA98), a new serotype of avian infectious bronchitis virus" *Virus Res*, Nov. 2001; 80(1-2):33-9.
Lee et al., "Typing of field isolates of infectious bronchitis virus based on the sequence of the hypervariable region in the S1 gene" *J Vet Diagn Invest*, Jul. 2003; 15(4):344-8.
Leyson, "Infectious Bronchitis Virus S1 Spike Gene Polymorphisms in the Arkansas DPI Vaccine Influence Minimum Infectious Dose and S1 Spike Protein Binding to Hose Cells" Dissertation Thesis, University of Georgia, Athens, GA, May 2016; 101 pages.
Leyson et al., "Polymorphisms in the S1 spike glycoprotein of Arkansas-type infectious bronchitis virus (IBV) show differential binding to host tissues and altered antigenicity" *Virology*, Nov. 2016; 498:218-25, Epub Sep. 15, 2016.
Leyson et al., "Minimum Infectious Dose Determination of the ArkDPI Infectious bronchitis Virus Vaccine Delivered by Hatchery Spray Cabinet" *Avian Dis*. Mar. 2017; 61(1):123-7.
Li et al., "Recombinant duck enteritis viruses expressing major structural proteins of the infectious bronchitis virus provide protection against infectious bronchitis in chickens" *Antiviral Res*, Jun. 2016; 130:19-26. Epub Mar. 2, 2016.
Lohr, "Infectious bronchitis agar-gel precipitin test—use of infected allantoic fluid as antigen" *Avian Dis*, Apr.-Jun. 1980; 24(2):463-7.
Lohr, "Diagnosis of infectious bronchitis (IB) by examination of tracheal mucus for IB-precipitating antigens" *Avian Dis*, Oct.-Dec. 1981; 25(4):1058-64.
Masters, "The molecular biology of coronaviruses" *Adv Vir Res*, 2006; 66:193-292.
McKinley et al., "Avian coronavirus infectious bronchitis attenuated live vaccines undergo selection of subpopulations and mutations following vaccination" *Vaccine*, Mar. 4, 2008; 26(10):1274-84, Epub Jan. 18, 2008.
Moore et al., "Identification of amino acids involved in a serotype and neutralization specific epitope within the si subunit of avian infectious bronchitis virus" *Arch Virol*, 1997; 142(11):2249-56.
Morgan et al., "Protection of chickens from Newcastle and Marek's diseases with a recombinant herpesvirus of turkeys vaccine expressing the Newcastle disease virus fusion protein" *Avian Dis*, Oct.-Dec. 1992; 36(4):858-70.
Ndegwa et al., "The proportion of specific viral subpopulations in attenuated Arkansas Delmarva poultry industry infectious bronchitis vaccines influences vaccination outcome" *Avian Dis*, Dec. 2012; 56(4):642-53.
Ndegwa et al., "Comparison of Vaccine Subpopulation Selection, Viral Loads, Vaccine Virus Persistence in Trachea and Cloaca, and Mucosal Antibody Responses After Vaccination with Two Different Arkansas Delmarva Poultry Industry-Derived Infectious Bronchitis Virus Vaccines" *Avian Dis*, Mar. 2014; 58(1):102-10.
Nix, Spike glycoprotein S-1 subunit, partial [Avian infectious bronchitis virus], Gen Bank: AAF05304.1. Dep. Nov. 2, 1999.
Nix et al., "Emergence of subtype strains of the Arkansas serotype of infectious bronchitis virus in Delmarva broiler chickens" Avian Dis. Jul.-Sep. 2000; 44(3):568-81. Abstract only.
Phillips et al., "Changes in nonstructural protein 3 are associated with attenuation in avian coronavirus infectious bronchitis virus" *Virus Genes*, Feb. 2012; 44(1):63-74. Epub Sep. 10, 2011.
Promkuntod et al., "Contributions of the S2 spike ectodomain to attachment and host range of infectious bronchitis virus" *Virus Res*, Nov. 6, 2013; 177(2):127-37. Epub Sep. 13, 2013.

(56) References Cited

OTHER PUBLICATIONS

Promkuntod et al., "Mapping of the receptor-binding domain and amino acids critical for attachment in the spike protein of avian coronavirus infectious bronchitis virus" *Virology*, Jan. 5, 2014; 448:26-32, Epub Oct. 16, 2013.

Purswell et al., "Effects of system pressure and nozzle type on spray application of avian vaccines" *Appl Eng Agric*, Dec. 1, 2008; 24(6):785-9.

Reed and Muench, "A Simple Method of Estimating Fifty Per Cent Endpoints" *American J Hygiene*, May 1938, 27(3):493-7.

Roh et al., "Evaluation of Infectious Bronchitis Virus Arkansas-Type Vaccine Failure in Commercial Broilers" *Avian Dis*, Jun. 2013; 57(2):248-59.

Roh et al., "Detection of infectious bronchitis virus with the use of real-time quantitative reverse transcriptase-PCR and correlation with virus detection in embryonated eggs" *Avian Dis*, Sep. 2014; 58(3):398-403.

Roh et al., "Hatchery spray cabinet administration does not damage avian coronavirus infectious bronchitis virus vaccine based on analysis by electron microscopy and virus titration" *Avian Dis*, Mar. 2015; 59(1):149-52.

Tatusova et al., "BLAST 2 Sequences, a new tool for comparing protein and nucleotide sequences" *FEMS Microbiol Lett*, May 15, 1999; 174(2):247-50.

Terregino et al., "Pathogenicity of a QX strain of infectious bronchitis virus in specific pathogen free and commercial broiler chickens, and evaluation of protection induced by a vaccination programme based on the Ma5 and 4/91 serotypes" *Avian Pathol*, Oct. 2008; 37(5):487-93.

Toro et al., "Epidemiological and experimental evidence for immunodeficiency affecting avian infectious bronchitis" *Avian Pathol*, Dec. 2006; 35(6):455-64.

Toro et al., "Genetic diversity and selection regulates evolution of infectious bronchitis virus" *Avian Dis*, Sep. 2012; 56(3):449-55.

Toro et al., "Infectious bronchitis virus S2 expressed from recombinant virus confers broad protection against challenge" *Avian Dis*, Mar. 2014; 58(1):83-9.

Toro et al., "S1 of distinct IBV population expressed from recombinant adenovirus confers protection against challenge" *Avian Dis*, Jun. 2014; 58(2):211-5.

Toro et al., "Cross-protection by infectious bronchitis viruses under controlled experimental conditions" *Avian Dis*, Dec. 2015; 59(4):532-6.

USDA Code of Federal Regulations, Title 9, Ch. I "Statute 113.327: Bronchitis Vaccine" Jan. 1, 2011 Edition, in USDA Animal and Plant Health Inspection Service, USDA, Washington D.C., 2011, p. 776-778.

Vagnozzi et al., "Protection induced by commercially available live-attenuated and recombinant viral vector vaccines against infectious laryngotracheitis virus in broiler chickens" *Avian Pathol*, 2012; 41(1):21-31.

Van Santen and Toro, "Rapid selection in chickens of subpopulations within ArkDPI-derived infectious bronchitis virus vaccines" *Avian Pathol*, Jun. 2008; 37(3):293-306.

Wang et al., "Isolation and identification of glandular stomach type IBV (QX IBV) in chickens" Chinese Journal of Animal Quarantine, 1998; 15(1):1-3. Abstract only. Retrieved from the Internet: <cabdirect.org/cabdirect/abstract/19992201828>. Retrieved on Jan. 4, 2019, 1 page.

Wickramasinghe et al., "Binding of Avian Coronavirus Spike Proteins to Host Factors Reflects Virus Tropism and Pathogenicity" *J Virol*, Sep. 2011; 85(17):8903-12.

Wickramasinghe et al., "The avian coronavirus spike protein" *Virus Res*, Dec. 19, 2014; 194:37-48, Epub Oct. 17, 2014.

Yan et al., "Protection of chickens against infectious bronchitis virus with a multivalent DNA vaccine and boosting with an inactivated vaccine" *J Vet Sci*, 2013; 14(1):53-60. Epub Feb. 5, 2013.

Yang et al., "The protective immune response against infectious bronchitis virus induced by multi-epitope based peptide vaccines" *Biosci Biotechnol Biochem*, Jul. 2009; 73(7):1500-4, Epub Jul. 7, 2009.

Yang et al., "Recombinant infectious bronchitis virus (IBV) H120 vaccine strain expressing the hemagglutinin-neuraminidase (HN) protein of Newcastle disease virus (NDV) protects chickens against IBV and NDV challenge" *Arch Virol*, May 2016; 161(5):1209-16, Epub Feb. 12, 2016.

Yin et al., "Immunogenicity and protective efficacy of recombinant fusion proteins containing spike protein of infectious bronchitis virus and hemagglutinin of H3N2 influenza virus in chickens" *Virus Res*, Sep. 2, 2016; 223:206-12, Epub Aug 3.

Yu et al., "Characterization of three infectious bronchitis virus isolates from China associated with proventriculus in vaccinated chickens" *Avian Dis*, Apr.-Jun. 2001; 45(2):416-24.

Zhao et al., "Genomic characteristics and changes of avian infectious bronchitis virus strain CK/CH/LDL/97I after serial passages in chicken embryos" *Intervirology*, 2014; 57(6):319-30, Epub Aug. 29, 2014.

FIG 9A

ATGTTGGTGAAGTCACTGTTTCTAGTGACCATTTTGTTTGCACTATGTAGTGCTAATTTATATGACAACGA
ATCTTTTGTGTATTACTACCAGAGTGCTTTTAGGCCAGGACATGGTTGGCATTTACATGGAGGTGCTTAT
GCAGTAGTTAATGTGTCTAGTGAAAATAATAATGCAGGTACTGCCCCAAGTTGCACTGCTGGTGCTATTG
GCTACAGTAAGAATTTCAGTGCGGCCTCAGTAGCCATGACTGCACCACTAAGTGGTATGTCATGGTCTG
CCTCATCTTTTTGTACAGCTCACTGTAATTTTACTTCTTATATAGTGTTTGTTACACATTGTTTTAAGAACG
GATCTAATAGTTGTCCTTTGACAGGTCTTATTCCAAGCGGTTATATTCGTATTGCTGCTATGAAACATGGA
AGTGCTACGCCTGGTCACTTATTTTATAACTTAACAGTTTCTGTGACTAAATATCCTAAGTTTAGATCGCT
ACAATGTGTTAATAATCATACTTCTGTATATTTAAATGGTGACCTTGTTTTCACATCTAACTATACTGAAG
ATGTTGTAGCTGCAGGTGTCCATTTTAAAAGTGGTGGACCTATAACTTATAAAGTTATGAGAGAGGTTA
AAGCCTTGGCTTATTTTGTCAATGGTACTGCACATGATGTCATTCTATGTGATGACACACCTAGAGGTTT
GTTAGCATGCCAATATAATACTGGCAATTTTTCAGATGGCTTCTATCCTTTTACTAATACTAGTATTGTTAA
GGATAAGTTTATTGTTTATCGTGAAAGTAGTGTCAATACTACTTTGACATTAACTAATTTCACGTTTAGTA
ATGAAAGTGGTGCCCCTCCTAATACAGGTGGTGTTGACAGTTTTATTTTATACCAGACACAAACAGCTCA
GAGTGGTTATTATAATTTTAATTTTTCATTTCTGAGTAGTTTTGTTTATAGGGAAAGTAATTATATGTATG
GATCTTACCATCCACGTTGTAGTTTTAGACCTGAAACCCTTAATGGTTTGTGGTTTAATTCCCTTTCTGTTT
CATTAACATACGGTCCCATTCAAGGTGGTTGTAAGCAATCTGTATTTAATGGTAAAGCAACTTGTTGTTA
TGCTTATTCATACGGAGGACCTCATGCTTGTAAAGGTGTCTATAGAGGTGAGCTAACACAGCATTTTGAA
TGTGGTTTGTTAGTTTATGTTACTAAGAGCGATGGCTCCCGTATACAAACTGCAACACAACCACCTGTAT
TAACCCAAAATTTTTATAATAACATCACTTTAGGTAAGTGTGTTGATTATAATGTTTATGGTAGAACTGGA
CAAGGTTTTATTACTAATGTAACTGATTTAGCTACTTCTCATAATTACTTAGCGGATGGAGGATTAGCTAT
TTTAGATACATCTGGTGCCATAGACATCTTCGTTGTACAAGGTGAATATGGCCCTAACTACTATAAGGTT
AATCTATGTGAAGATGTTAACCAACAGTTTGTAGTTTCTGGTGGTAAATTAGTAGGTATTCTCACTTCAC
GTAATGAAACTGGTTCTCAGCCTCTTGAAAACCAGTTTTACATTAAGATCACTAATGGAACACATCGTTCT
AGACGTTC

FIG 9B

MLVKSLFLVTILFALCSANLYDNESFVYYYQSAFRPGHGWHLHGGAYAVVNVSSENNNAGTAPSCTAGAIGY
SKNFSAASVAMTAPLSGMSWSASSFCTAHCNFTSYIVFVTHCFKNGSNSCPLTGLIPSGYIRIAAMKHGSATP
GHLFYNLTVSVTKYPKFRSLQCVNNHTSVYLNGDLVFTSNYTEDVVAAGVHFKSGGPITYKVMREVKALAYF
VNGTAHDVILCDDTPRGLLACQYNTGNFSDGFYPFTNTSIVKDKFIVYRESSVNTTLTLTNFTFSNESGAPPNT
GGVDSFILYQTQTAQSGYYNFNFSFLSSFVYRESNYMYGSYHPRCSFRPETLNGLWFNSLSVSLTYGPIQGGC
KQSVFNGKATCCYAYSYGGPHACKGVYRGELTQHFECGLLVYVTKSDGSRIQTATQPPVLTQNFYNNITLGK
CVDYNVYGRTGQGFITNVTDLATSHNYLADGGLAILDTSGAIDIFVVQGEYGPNYYKVNLCEDVNQQFVVSG
GKLVGILTSRNETGSQPLENQFYIKITNGTHRSRR

SEQUENCE LISTING

```
<160> NUMBER OF SEQ ID NOS: 5

<210> SEQ ID NO 1
<211> LENGTH: 1631
<212> TYPE: DNA
<213> ORGANISM: Infectious bronchitis virus

<400> SEQUENCE: 1
atgttggtga agtcactgtt tctagtgacc attttgtttg cactatgtag tgctaattta      60
tatgacaacg aatcttttgt gtattactac cagagtgctt ttaggccagg acatggttgg     120
catttacatg gaggtgctta tgcagtagtt aatgtgtcta gtgaaaataa taatgcaggt     180
actgccccaa gttgcactgc tggtgctatt ggctacagta agaatttcag tgcggcctca     240
gtagccatga ctgcaccact aagtggtatg tcatggtctg cctcatcttt ttgtacagct     300
cactgtaatt ttacttctta tatagtgttt gttacacatt gttttaagaa cggatctaat     360
agttgtcctt tgacaggtct tattccaagc ggttatattc gtattgctgc tatgaaacat     420
ggaagtgcta cgcctggtca cttattttat aacttaacag tttctgtgac taaatatcct     480
aagtttagat cgctacaatg tgttaataat catacttctg tatatttaaa tggtgacctt     540
```

-continued

```
gttttcacat ctaactatac tgaagatgtt gtagctgcag gtgtccattt taaaagtggt      600
ggacctataa cttataaagt tatgagagag gttaaagcct tggcttattt tgtcaatggt      660
actgcacatg atgtcattct atgtgatgac acacctagag gtttgttagc atgccaatat      720
aatactggca attttttcaga tggcttctat cctttttacta atactagtat tgttaaggat     780
aagtttattg tttatcgtga agtagtgtc aatactactt tgacattaac taatttcacg      840
tttagtaatg aaagtggtgc ccctcctaat acaggtggtg ttgacagttt tattttatac      900
cagacacaaa cagctcagag tggttattat aattttaatt tttcatttct gagtagtttt      960
gtttataggg aaagtaatta tatgtatgga tcttaccatc cacgttgtag ttttagacct     1020
gaaacccttta atggtttgtg gtttaattcc ctttctgttt cattaacata cggtcccatt     1080
caaggtggtt gtaagcaatc tgtatttaat ggtaaagcaa cttgttgtta tgcttattca     1140
tacggaggac ctcatgcttg taaggtgtc tatagaggtg agctaacaca gcattttgaa       1200
tgtggtttgt tagtttatgt tactaagagc gatggctccc gtatacaaac tgcaacacaa     1260
ccacctgtat taacccaaaa ttttttataat aacatcactt taggtaagtg tgttgattat    1320
aatgttatg gtagaactgg acaaggtttt attactaatg taactgattt agctacttct       1380
cataattact tagcggatgg aggattagct attttagata catctggtgc catagacatc     1440
ttcgttgtac aaggtgaata tggccctaac tactataagg ttaatctatg tgaagatgtt     1500
aaccaacagt ttgtagtttc tggtggtaaa ttagtaggta ttctcacttc acgtaatgaa     1560
actggttctc agcctcttga aaaccagttt tacattaaga tcactaatgg aacacatcgt     1620
tctagacgtt c                                                          1631
```

<210> SEQ ID NO 2
<211> LENGTH: 543
<212> TYPE: PRT
<213> ORGANISM: Infectious bronchitis virus

<400> SEQUENCE: 2

```
Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Asn Gly Ser Asn Ser Cys Pro Leu Thr Gly Leu Ile
        115                 120                 125

Pro Ser Gly Tyr Ile Arg Ile Ala Ala Met Lys His Gly Ser Ala Thr
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175
```

```
Asn Gly Asp Leu Val Phe Thr Ser Asn Tyr Thr Glu Asp Val Val Ala
            180                 185                 190

Ala Gly Val His Phe Lys Ser Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
            245                 250                 255

Ile Val Lys Asp Lys Phe Ile Val Tyr Arg Glu Ser Val Asn Thr
        260                 265                 270

Thr Leu Thr Leu Thr Asn Phe Thr Phe Ser Asn Glu Ser Gly Ala Pro
    275                 280                 285

Pro Asn Thr Gly Gly Val Asp Ser Phe Ile Leu Tyr Gln Thr Gln Thr
290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
            325                 330                 335

Ser Phe Arg Pro Glu Thr Leu Asn Gly Leu Trp Phe Asn Ser Leu Ser
        340                 345                 350

Val Ser Leu Thr Tyr Gly Pro Ile Gln Gly Gly Cys Lys Gln Ser Val
    355                 360                 365

Phe Asn Gly Lys Ala Thr Cys Cys Tyr Ala Tyr Ser Tyr Gly Gly Pro
370                 375                 380

His Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
            405                 410                 415

Thr Ala Thr Gln Pro Pro Val Leu Thr Gln Asn Phe Tyr Asn Asn Ile
        420                 425                 430

Thr Leu Gly Lys Cys Val Asp Tyr Asn Val Tyr Gly Arg Thr Gly Gln
    435                 440                 445

Gly Phe Ile Thr Asn Val Thr Asp Leu Ala Thr Ser His Asn Tyr Leu
450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
            485                 490                 495

Cys Glu Asp Val Asn Gln Gln Phe Val Val Ser Gly Gly Lys Leu Val
        500                 505                 510

Gly Ile Leu Thr Ser Arg Asn Glu Thr Gly Ser Gln Pro Leu Glu Asn
    515                 520                 525

Gln Phe Tyr Ile Lys Ile Thr Asn Gly Thr His Arg Ser Arg Arg
530                 535                 540
```

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide Primer

<400> SEQUENCE: 3

```
gcttttgagc ctagcgtt                                                    18

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 4
gccatgttgt cactgtctat tg                                               22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 5
caccaccaga acctgtcacc tc                                               22
```

LIVE ATTENUATED ARKANSAS SEROTYPE INFECTIOUS BRONCHITIS VIRUS VACCINE

CONTINUING APPLICATION DATA

This application is a continuation of U.S. Nonprovisional application Ser. No. 16/410,340, filed May 13, 2019, which is a divisional of U.S. Nonprovisional application Ser. No. 15/880,972, filed Jan. 26, 2018, which claims the benefit of U.S. Provisional Application Ser. No. 62/451,335, filed Jan. 27, 2017, and U.S. Provisional Application Ser. No. 62/583,270, filed Nov. 8, 2017, which are incorporated by reference herein in their entireties.

SEQUENCE LISTING

This application contains a Sequence Listing electronically submitted via EFS-Web to the United States Patent and Trademark Office as an ASCII text file entitled "SequenceList-0269-US02_ST25.txt" having a size of 8 kilobytes and created on Dec. 22, 2020. The information contained in the Sequence Listing is incorporated by reference herein.

BACKGROUND

The Arkansas serotype of infectious bronchitis virus (IBV) is the most isolated type of IBV from commercial poultry. This is due to the heavy use of the currently available Ark-type vaccine in use in the industry, ArkDPI. The ArkDPI vaccine was developed from an isolate from the DelMarVa peninsula in the late 1970's and has been the only available Ark-type vaccine since that time. It has previously been shown that this vaccine is not efficacious at protecting chickens from a pathogenic Ark-type challenge, it does not infect and replicate well in chicks when mass applied and contains multiple genetic subpopulations that cause the vaccine to erratically reappear in vaccinated flocks and transmit to non-vaccinated flocks. For these reasons, new Arkansas type IBV vaccines are needed in the commercial poultry industry.

SUMMARY OF THE INVENTION

The present invention includes an infectious bronchitis virus (IBV) isolate, wherein the IBV isolate is the IBV isolate ArkGA p60 deposited with the American Type Culture Collection (ATCC®), 10801 University Boulevard, Manassas, Va. 20110-2209, USA, on Feb. 7, 2017, under Patent Designation PTA-123783.

The present invention includes an attenuated infectious bronchitis virus (IBV) isolate of the Arkansas serotype, the attenuated IBV isolate having an S1 glycoprotein subunit comprising an amino acid sequence comprising at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO: 2. In some embodiments, the S1 glycoprotein subunit includes an asparagine residue at amino acid position 117 and/or a histidine residue at amino acid position 386.

The present invention includes an attenuated IBV isolate of the Arkansas serotype, the attenuated IBV isolate having an S1 glycoprotein subunit encoded by a nucleotide sequence comprising at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO: 1. In some embodiments, the encoded S1 glycoprotein subunit includes an asparagine residue at amino acid position 117 and/or a histidine residue at amino acid position 386.

The present invention includes an attenuated IBV isolate of the Arkansas serotype, the attenuated IBV isolate having an S1 glycoprotein subunit comprising an amino acid sequence comprising at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the Ark99 S1 glycoprotein subunit. In some embodiments, the S1 glycoprotein subunit of the attenuated IBV isolate includes an asparagine residue at amino acid position 117 and/or a histidine residue at amino acid position 386.

In some aspects, an IBV isolate as described herein may be lyophilized or frozen.

The present invention includes a composition comprising an IBV isolate. In some aspects, the composition further includes a pharmaceutically acceptable carrier. In some aspects, the composition is formulated for mucosal administration. In some aspects, the composition is formulated for intranasal, intraocular, or oral administration. In some aspects, the composition is formulated for spraying or aerolizing. In some aspects, the composition further includes other viral material.

The present invention includes a vaccine including an attenuated IBV isolate as described herein. In some aspects, the vaccine reduces the susceptibility of a bird of the order Galliformes to disease induced by the Arkansas serotype of IBV.

The present invention includes a method of producing an immune response to the IBV virus in poultry, the method including administering an IBV isolate as described herein, a composition as described herein, or a vaccine of claim as described herein to poultry. In some aspects, the immune response is to an IBV virus of the Arkansas serotype. In some aspects, poultry includes chicken or turkey. In some aspects, the composition is administered by spraying.

The present invention includes a method of preventing an IBV infection in poultry, the method including administering an IBV isolate as described herein, a composition as described herein, or a vaccine as described herein to poultry. In some aspects, the IBV infection is of the Arkansas serotype. In some aspects, poultry includes chicken or turkey. In some aspects, the composition is administered by spraying.

The present invention includes an isolated S1 polypeptide having at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:2. In some embodiments, the S1 glycoprotein subunit includes an asparagine residue at amino acid position 117 and/or a histidine residue at amino acid position 386.

The present invention includes an isolated nucleotide sequence encoding an IBV S1 glycoprotein subunit, wherein the nucleotide sequence has at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:1. In some embodiments, the encoded S1 glycoprotein subunit includes an asparagine residue at amino acid position 117 and/or a histidine residue at amino acid position 386.

The present invention includes a vector including an isolated nucleotide sequence as described herein.

The present invention includes a kit including an attenuated IBV isolate as described herein, a composition as described herein, a vaccine as described herein, a S1 polynucleotide as described herein, a nucleotide sequence as described herein, and/or a vector as described herein. In some aspects, the kit further includes printed instructions and/or the contents of the kit are contained within packaging material.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.).

The terms "comprises" and variations thereof do not have a limiting meaning where these terms appear in the description and claims.

Unless otherwise specified, "a," "an," "the," and "at least one" are used interchangeably and mean one or more than one.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 3A presents clinical signs. FIG. 3B presents ciliostasis scores. FIG. 3C and FIG. 3D present relative viral loads. Clinical sign scores were calculated based on severity where 0=negative, 1=mild signs, 2=watery eyes and some mucus in the nares, and 3=watery eyes, mucus in the nares and trachea (tracheal rales). Ciliostasis scores were calculated as previously described where a score above 50 is considered passing. Ct=cycle threshold; Statistical analysis: * indicates statistical differences ($p<0.0001$) in Ct values compared to challenged controls.

FIG. 7A presents clinical signs. FIG. 7B presents ciliostasis scores. FIG. 7C and FIG. 7D present relative viral loads. Clinical sign scores were calculated based on severity where 0=negative, 1=mild signs, 2=watery eyes and some mucus in the nares, and 3=watery eyes, mucus in the nares and trachea (tracheal rales). Ciliostasis scores were calculated as previously described where a score above 50 is considered passing. Ct=cycle threshold. Statistical analysis: * indicates statistical differences ($p<0.01$ or $0.0001$) in Ct values compared to challenged controls.

FIGS. 9A and 9B. FIG. 9A presents the nucleotide sequence (SEQ ID NO: 1) of the S1 subunit of the spike genes for both the P50 ArkGA IBV and the P60 ArkGA IBV isolates. FIG. 9B presents the deduced amino acid sequence (SEQ ID NO: 2) of the S1 subunit for both the P50 ArkGA IBV and the P60 ArkGA IBV isolates.

DETAILED DESCRIPTION

Figure 1:
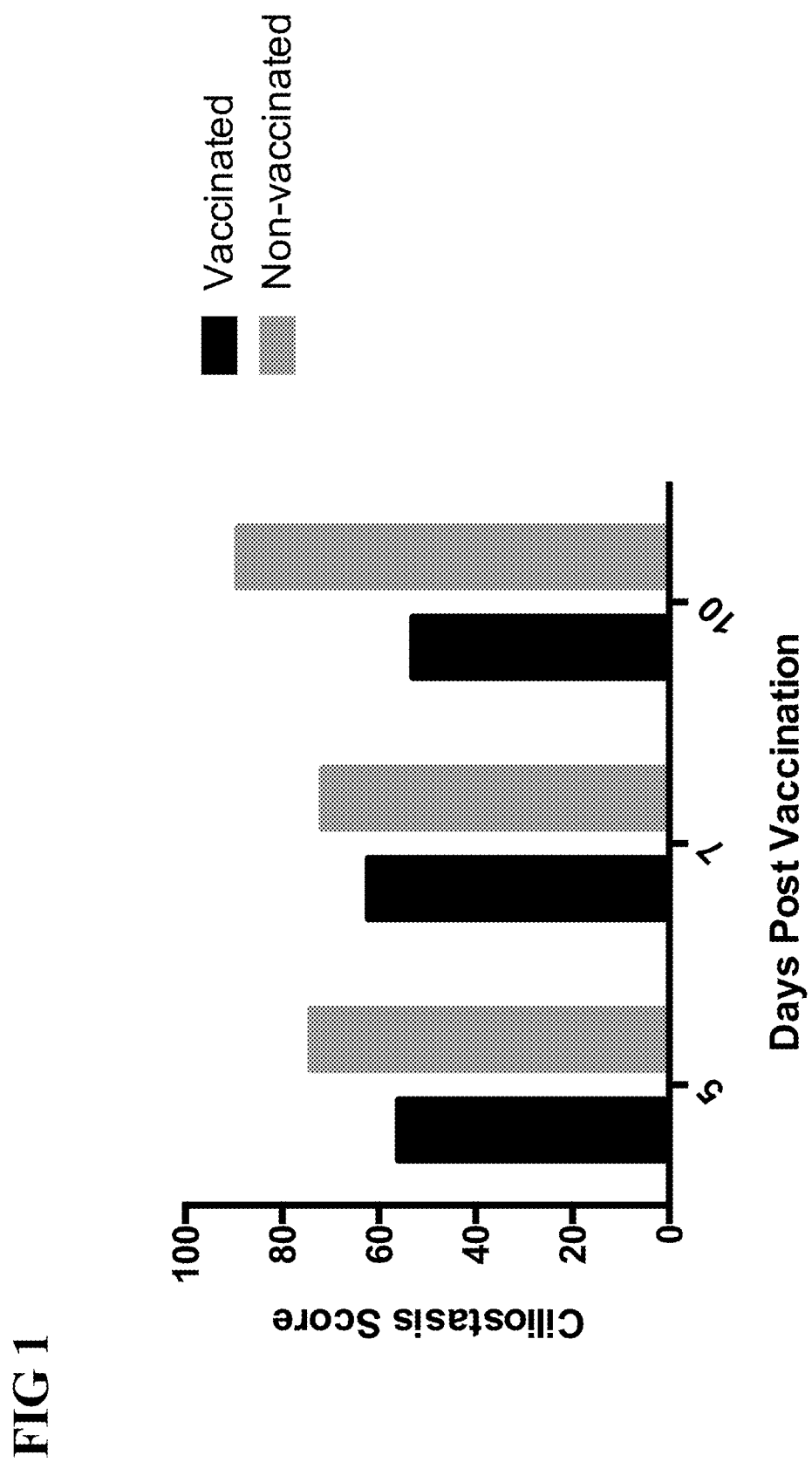
FIG. 1. Comparison of ArkGA P1 vaccinated and non-vaccinated ciliostasis scores in SPF chickens during safety testing of Experiment 1. Ciliostasis scores were calculated as previously described where a score above 50 is considered passing.
Figure 2B:
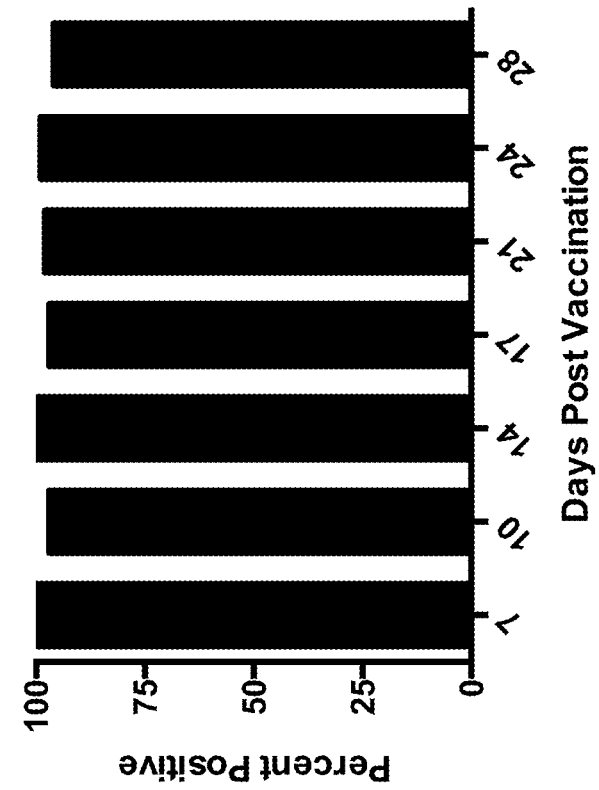
FIGS. 2A and 2B. Viral load in chickens (FIG. 2A) and vaccine coverage (FIG. 2B) after spray vaccination with ArkGA P1 vaccine candidate of Experiment 2. Ct=cycle threshold.
Figure 2A:
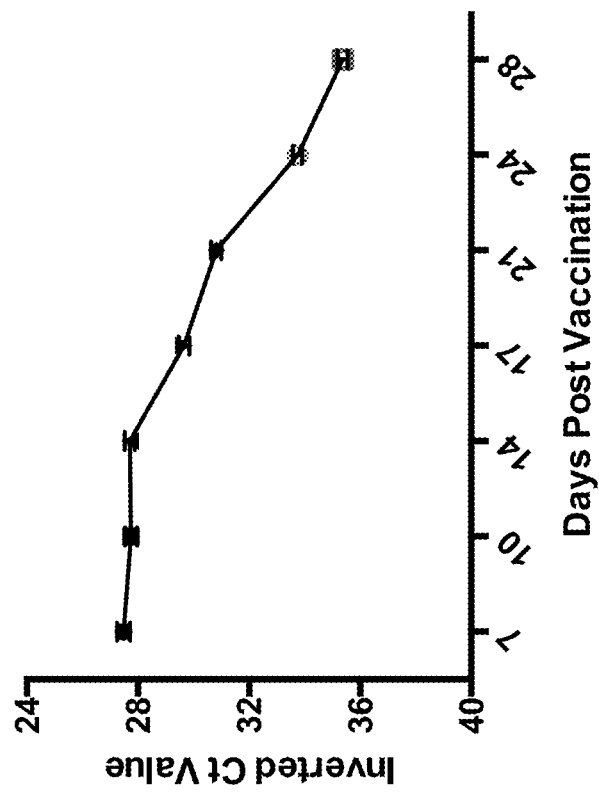
Figure 3A:
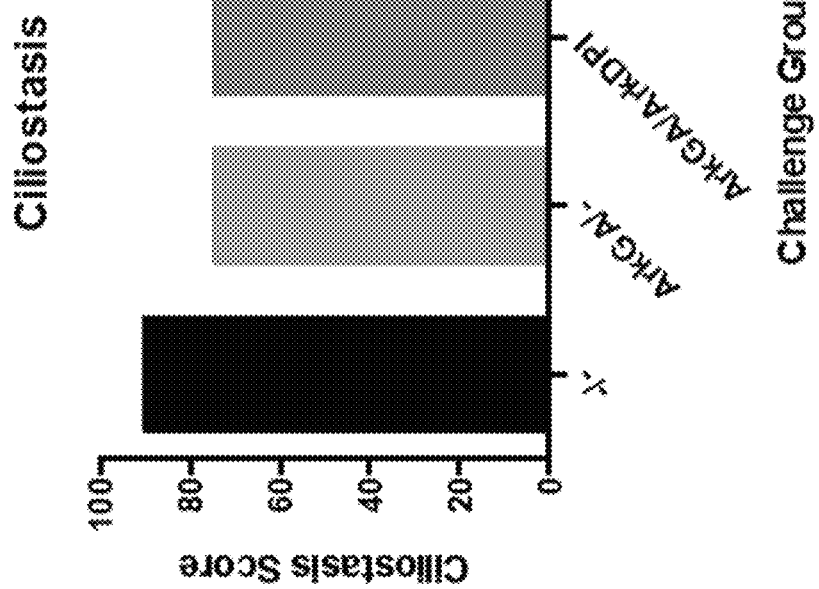
FIGS. 3A-3D. Clinical signs, ciliostasis scores, and viral loads in chickens post-challenge of Experiment 2.
Figure 3B:
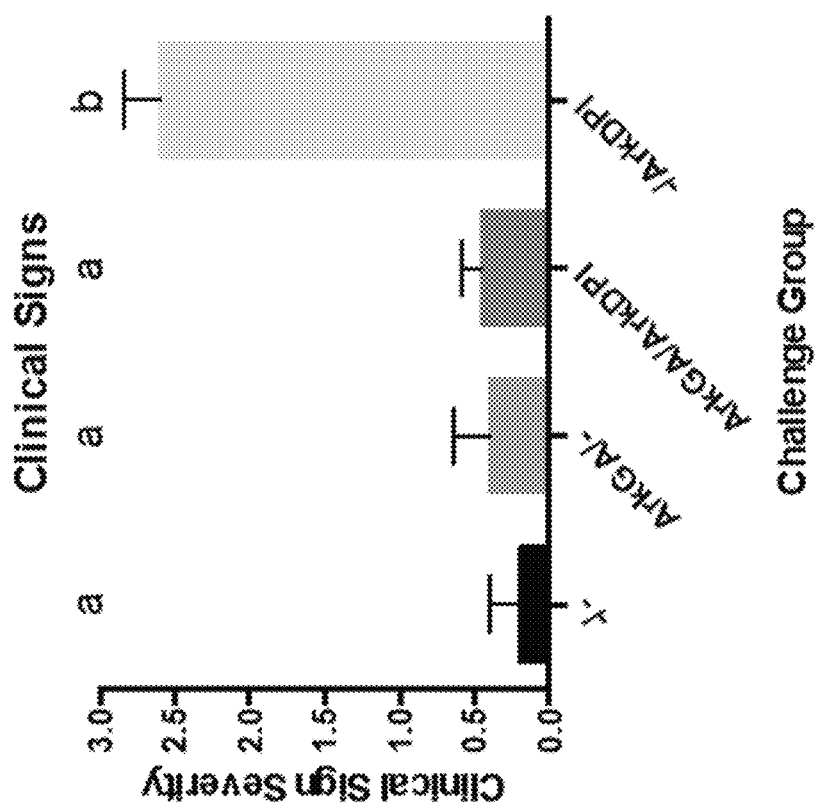
Figure 3C:
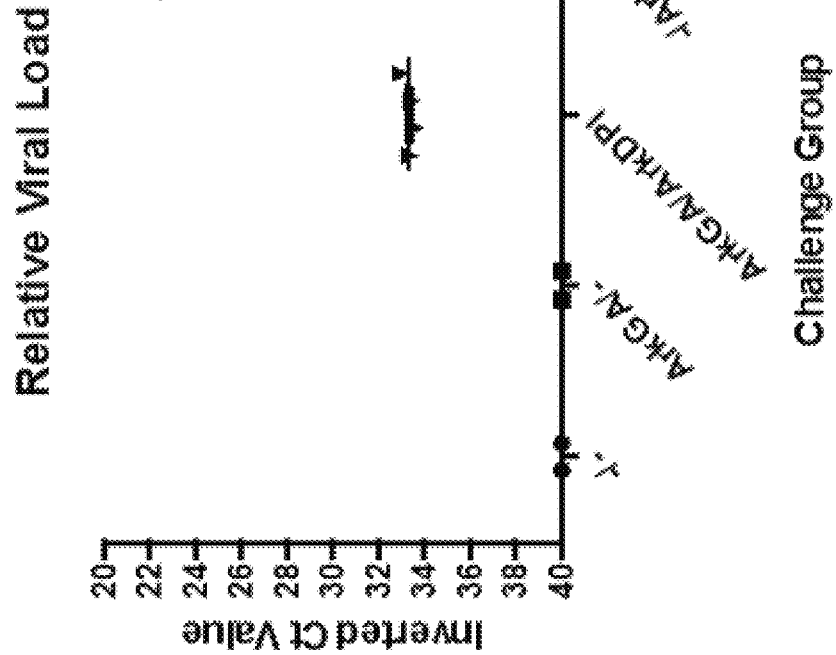
Figure 3D:
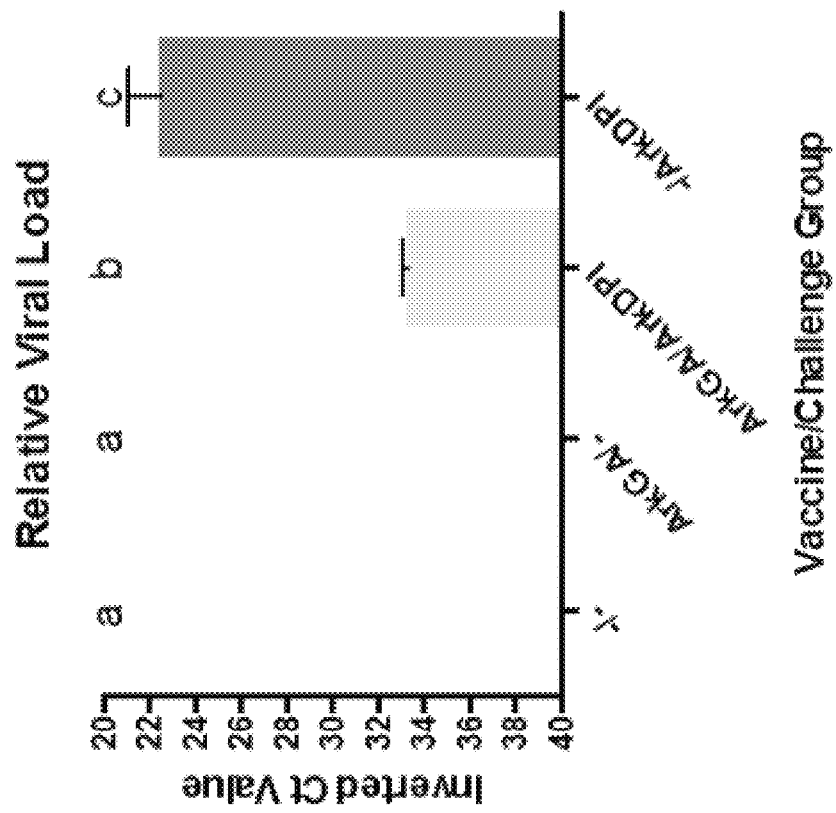
Figure 4A:
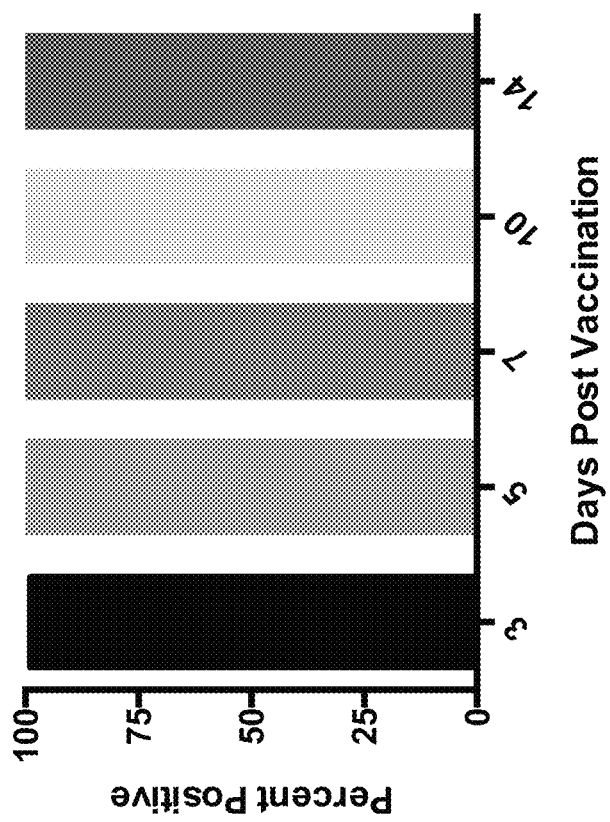
FIGS. 4A and 4B. Viral loads in chickens (FIG. 4A) and vaccine coverage (FIG. 4B) post-vaccination with ArkGA P20 of Experiment 3, Trial 1. Ct=cycle threshold.
Figure 4B:
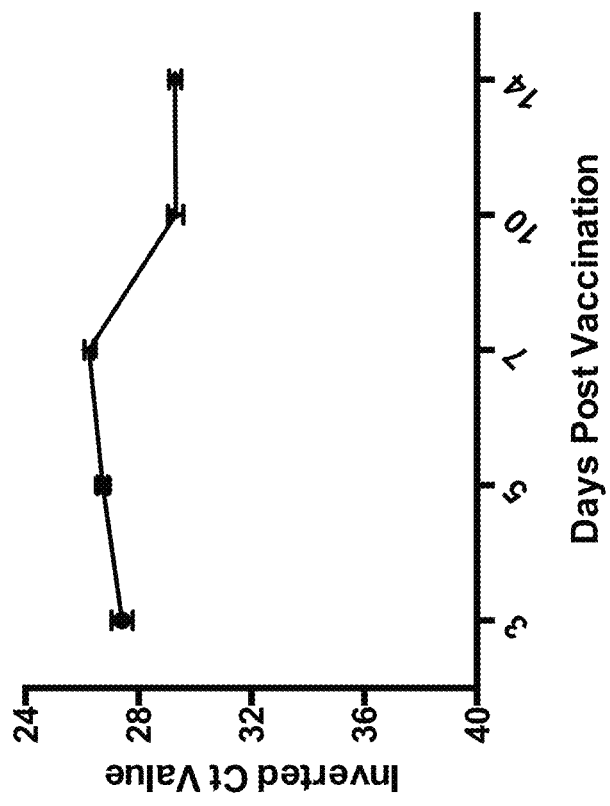
Figure 5A:
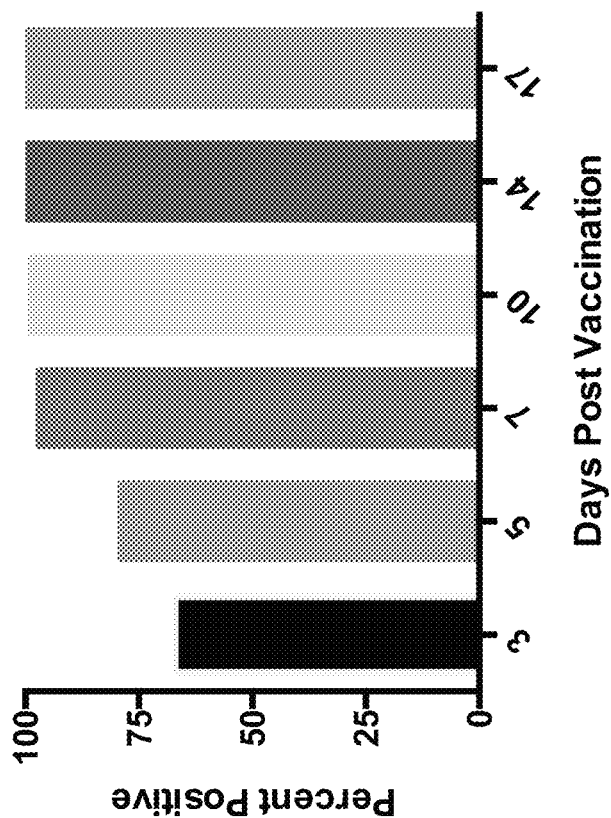
FIGS. 5A and 5B. Viral loads in chickens (FIG. 5A) and vaccine coverage (FIG. 5B) post-vaccination with ArkGA P40 of Experiment 3, Trial 2. Ct=cycle threshold.
Figure 5B:
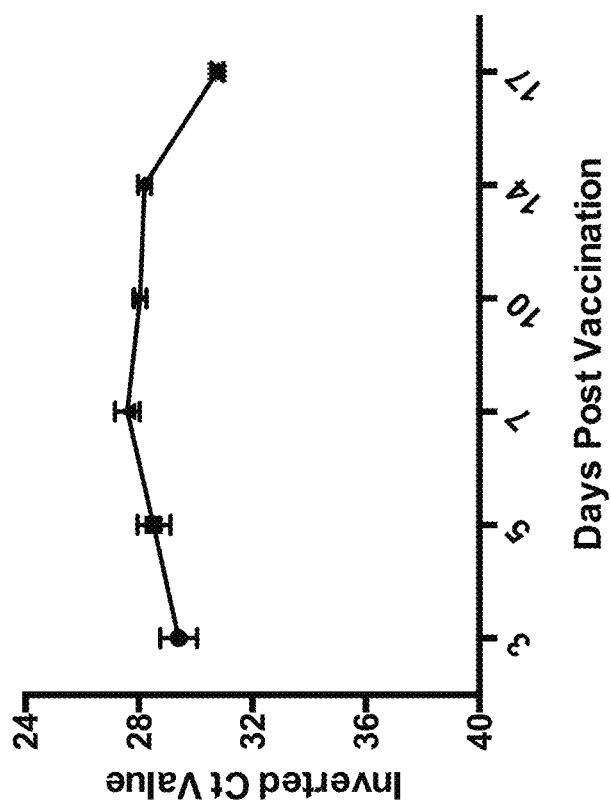

The present invention relates to new materials and methods in the field of poultry virology, particularly in the field of the infectious bronchitis virus (IBV).

Avian IBV is a gammacoronavirus that causes an economically significant upper respiratory tract disease in chickens (Economic Data, in U.S. Poultry & Egg Association, 2016). Because of its prevalence and infectivity, nearly all commercial poultry in the U.S. are vaccinated against IBV in a serotype-specific manner (Cavanagh, 2007, *Veterinary Research;* 38:281-297). Of the vaccines used in the United States, the Arkansas Delmarva Poultry Industry (ArkDPI) serotype vaccine has been shown to be highly variable in its protective ability, and is frequently isolated from vaccinated chicks (Jackwood et al., 2005, *Avian Dis;* 49:614-618, Ndegwa et al., 2014, *Avian Dis;* 58:102-110, and Toro et al., 2006, *Avian Pathol;* 35:455-464). It has been shown that the ArkDPI vaccine has an atypical infection and replication pattern when mass applied by spray, and previous data suggests that levels of vaccine virus infection post-vaccination only reach 15-25% (Jackwood et al., 2009, *Avian Dis;* 53:175-183). Multiple replication cycles also occur in the bird (indicated by viral load in chicks), resulting in "rolling" reactions at different time points post-vaccination. Earlier work has shown that to achieve an adequate infection rate with ArkDPI post-vaccination and eliminate rolling replication cycles, a 100× dose by spray is required (Leyson et al., 2016, "Minimum Infectious Dose Determination of the ArkDPI Infectious bronchitis Virus Vaccine Delivered by Hatchery Spray Cabinet," *Avian Dis*, and Roh et al., 2013, *Avian Dis;* 57:248-259).

The atypical infection and cycling of ArkDPI is a product of the multiple minor genetic subpopulations in the vaccine bottle. It has been previously shown that IBV vaccines of multiple serotypes contain genetic subpopulations and that these populations are often recovered in chickens after vaccination, though these vaccines show a typical infection and replication cycle and protect from challenge. With ArkDPI, the major population in the vaccine contains multiple, distinct amino acid changes in the spike protein, namely positions 43 and 344, that have been shown to be directly involved in spike protein binding to host tissues as well as being implicated in the development of immunity after vaccination (Leyson et al. 2016, *Virology;* 498:218-225, and Ndegwa et al., 2014, *Avian Dis;* 58:102-110). The ArkDPI vaccine major population contains amino acids at these positions in the spike protein that increase binding affinity in the embryonated egg, but decrease binding affinity to mature chicken cells. This allows the minor populations to infect and replicate in chickens (Leyson et al. 2016, *Virology;* 498:218-225, and Van Santen and Toro, 2008, *Avian Pathol;* 37:293), but they are only a fraction of the total genetic population contained in the vaccine bottle. Thus, the infection rate is very low and the time to reach peak infection and replication is delayed. For these reasons, chickens do not develop adequate immunity after ArkDPI vaccination. Although using one of the viral subpopulations directly as a vaccine will induce a protective immune response, these populations cannot be maintained through multiple passages in embryonated chicken eggs as is required to propagate IBV vaccine.

The amino acid and nucleotide sequence of the S1 portion of the spike gene of ArkDPI are included within the complete genome sequence found as Accession No. GQ504721, Version GQ504721.2 (9 Jul. 2012). See also, Phillips et al., "Changes in nonstructural protein 3 are associated with attenuation in avian coronavirus infectious bronchitis virus," *Virus Genes* 44 (1), 63-74 (2012).

While ArkDPI is the only commercially available Ark-type IBV vaccine today, it is not the only Ark-type IBV vaccine ever produced. Arkansas 99 (Ark99) infectious bronchitis virus is the same serotype as ArkDPI, and was the first Ark-type virus to be attenuated for use as a vaccine. When originally mass applied in the field, it caused a severe vaccine reaction in young broilers, and was therefore discontinued when ArkDPI was produced (Fields, 1973, "Case Report: Arkansas 99, a New Infectious Bronchitis Serotype," *Avian Dis;* 17:659-661, and Johnson et al., 1973, *Avian Dis;* 17:518-523).

The cDNA sequence and the deduced amino acid sequence of the spike protein of the Ark99 infectious bronchitis virus are found as GenBank Accession No. L10384, Version L10384.1 (18 Apr. 1995). See also, Jia et al., "A novel variant of avian infectious bronchitis virus resulting from recombination among three different strains," *Arch Virol;* 140 (2), 259-271 (1995).

The present invention provides new attenuated isolates of the Arkansas serotype of IBV. Such attenuated isolates may be used as live attenuated vaccines for the vaccination of poultry against IBV. Attenuated isolates demonstrate limiting virulence. Any of various attenuation process known in the art may be used. For example, attenuated isolates may be obtained by passage through specific pathogen free (SPF) chicken embryos and/or by heat treatment. Examples of such attenuation processes include, but are not limited to, those described, for example, in WO 2009/143332 and U.S. Pat. No. 8,679,504 (each of which are hereby incorporated by reference in their entirety). For example, attenuated isolates may be obtained by passaging virulent isolates of the present invention in a culture on a suitable medium a sufficient number of times to reduce its pathogenicity while retaining its immunogenicity. A preferred medium for such passaging is a SPF embryonated egg. Inoculation of the eggs can be via the allantoic cavity, chorioallantoic membrane, yolk sac, amniotic cavity or even direct into the embryo. The virus can be passaged at regular intervals of from 7 hours up to 4 days. Commonly, passaging takes place between 16 to 36 hours, preferably every 24 hours. Alternatively, attenuation may also be achieved by passaging the isolate in avian cell culture, such as chick embryo kidney cells.

In some embodiments, an attenuated isolate of the Arkansas serotype of IBV includes a further attenuation of the Ark99 vaccine. Arkansas99 is one of the original Ark-type IBV isolates from Arkansas that was originally attenuated into a vaccine. The vaccine was efficacious, but was still very pathogenic—to the point where producers stopped using it because of the negative side effects. Such further attenuations of Ark99 may include, but are not limited to, attenuated isolates obtained by passage of a Ark99 vaccine viral isolate through embryonated eggs obtained after, for example, 50 or more passages, 60 or more passages, 70 or more passages, 80 or more passages, 85 or more passages, 90 or more passages, 95 or more passages, or 100 or more passages. Such further attenuated isolates may include, but are not limited to, attenuated isolates obtained by passage of a Ark99 vaccine viral isolate through embryonated eggs obtained after, for example, about 50 passages, about 60 passages, about 65 passages, about 70 passages, about 75 passages, about 80 passages, about 85 passages, about 90 passages, about 95 passages, or about 100 passages. Such an isolate may be obtained after, for example, 50 passages (P50), 60 passages (P60), 65 passages (P65), 70 passages (P70), 75 passages (P75), 80 passage (P80), or any number of passages from 1 to 150 (PN, wherein N is an integer from 50 to 150).

In some embodiments, an attenuated isolate of the Arkansas serotype of IBV includes an attenuation of the Ark99 vaccine virus by 50 passages, 60 passages, or 70 passages through embryonated eggs. In some embodiments, an attenuated isolate of the Arkansas serotype of IBV includes an attenuation of the Ark99 vaccine virus by 50 passages (P50). In some embodiments, an attenuated isolate of the Arkansas serotype of IBV includes an attenuation of the Ark99 vaccine virus by 60 passages (P60) through embryonated eggs.

In some embodiments, an attenuated isolate of the Arkansas serotype of IBV may be an ArkGA isolate, such as for example, an ArkGA P50 isolate (obtained with 50 passages of the Ark99 vaccine virus through embryonated eggs) or an ArkGA P60 isolate (obtained with 60 passages of the Ark99 vaccine virus through embryonated eggs).

An attenuated IBV isolate of the present invention may be deposited with the American Type Culture Collection (ATCC®) 10801 University Boulevard, Manassas, Va. 20110-2209, USA. Such a deposit may be in accordance with the Budapest Treaty on the International Recognition of the Deposit of Microorganisms for the Purposes of Patent Procedure.

For example, the present invention includes the ArkGA P40 isolate deposited at the ATCC under Patent Designation PTA-126834 on Oct. 21, 2020, and the ArkGA P60 isolate deposited at the ATCC under Patent Designation PTA-123783 on Feb. 7, 2017.

The enveloped IBV virus has a single stranded-positive sense RNA genome that codes for the viral RNA-dependent RNA-polymerase, three major structural proteins (the nucleocapsid, membrane, and spike (S) proteins), and numerous regulatory proteins (Masters, 2006, *Adv Vir Res;* 66:193-292). The spike glycoprotein of IBV is translated as a precursor protein (So) and then cleaved into two subunits, the N-terminal S1 glycoprotein and the C-terminal S2 glycoprotein by host cell serine proteases. The S1 and S2 glycoproteins mediate cell attachment, virus-cell membrane fusion, and play an important role in host cell specificity, forming club shaped projections on the surface of the virus. The S1 glycoprotein induces virus-neutralizing and hemagglutination-inhibiting antibodies.

The IBV virus has multiple serotypes, with more than 20 serotypes within IBV recognized worldwide (Lee and Jackwood, 2000, *Arch Virol;* 145:2135-48). New variant strains arise due to rapid recombination, insertions, deletions, or point mutation events, predominantly in the S1 spike protein gene. Along with the use of serologic based tests, PCR and partial sequencing of the S1 gene can be used to group and type IBV isolates. A few changes in the sequence of the spike glycoprotein can result in a new serotype. It has been documented that as little as a 5% difference in the S1 sequence of IBV can result in a loss of cross-protection between otherwise similar isolates (Cavanagh, 2003, *Avian Pathol;* 32:567-582). The sequence from the hypervariable regions of the IBV S1 gene often correlates well with virus neutralization tests and can be reliably used to serotype an IBV isolate (Lee et al., 2003, *J Vet Diagn Invest;* 15:344-348). In the S1 subunit, three hypervariable regions (HVR) have been identified, located within amino acids 38-67, 91-141, and 274-387 (see, for example, Cavanagh et al., 1988, *Virus Res;* 11:141-150; Koch et al., 1990, *J Gen Virol;* 71:1929-1935; and Moore et al., 1997, *Arch Virol;* 142: 2249-2256).

In some embodiments, an attenuated isolate of the Arkansas serotype of IBV includes an IBV viral isolate with a nucleotide sequence encoding an S1 polypeptide defined by the S1 polypeptide of the ArkGA P50 isolate and/or the Ark P60 isolate, as described herein. For example, the present invention includes an IBV viral isolate with an S1 polypeptide encoded be a nucleotide sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to SEQ ID NO:1. In some embodiments, the nucleotide sequence includes one or more differences from a naturally occurring Arkansas serotype IBV viral isolate. In some embodiments, the nucleotide sequence encodes an S1 polypeptide with an asparagine residue at amino acid position 117 and/or a histidine residue at amino acid position 386. The present invention includes IBV viral isolates with an S1 polypeptide encoded by SEQ ID NO:1.

In some embodiments, an attenuated isolate of the Arkansas serotype of IBV includes an IBV viral isolate with an S1 polypeptide having the amino acid sequence defined by the S1 polypeptide of the ArkGA P50 isolate and/or the Ark P60 isolate, as described herein. For example, the present invention includes an IBV viral isolate with an S1 polypeptide with an amino acid sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to SEQ ID NO:2. In some embodiments, the S1 polypeptide includes one or more differences from a naturally occurring Arkansas serotype IBV viral isolate. In some embodiments, the amino acid sequence of the S1 polypeptide includes an asparagine residue at amino acid position 117 and/or a histidine residue at amino acid position 386. The present invention includes an IBV viral isolate with an S1 polypeptide with the amino acid sequence SEQ ID NO:2.

The present invention includes a nucleotide sequence encoding an S1 polypeptide of a ArkGA isolate as described herein, including, for example, a polynucleotide sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the polynucleotide sequence SEQ ID NO:1. In some embodiments, the nucleotide sequence encoding an S1 polypeptide includes one or more differences from a naturally occurring viral isolate. In some embodiments, the S1 polypeptide includes an asparagine residue at amino acid position 117 and/or a histidine residue at amino acid position 386. The present invention includes a polynucleotide sequence including SEQ ID NO:1.

Sequence identity may be determined, for example, using BLAST analysis. "BLAST analysis" is intended to mean the nucleotide or protein sequence analysis program available from the United States National Center for Biotechnology, and as described in more detail herein.

The present invention includes polynucleotide sequences that hybridize to SEQ ID NO:1, or a complement thereof, under various stringency conditions, and fragments thereof. Stringency conditions include, but are not limited to, moderate and high stringency. High stringency hybridization conditions may be, for example, 6×SSC, 5×Denhardt, 0.5% sodium dodecyl sulfate (SDS), and 100 m/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes. The present invention includes polypeptides encoded by such hybridizing polynucleotide sequences.

A polynucleotide sequence may be DNA, RNA, or a modification thereof. A polynucleotide sequence may be single or double stranded, sense (positive) or antisense (negative) sequences.

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, or about 700, nucleotides in length. Such a portion may be about 10 nucleotides to about 100 nucleotides in length, including but not limited to, about 14 to about 40 nucleotides in length. Fragments of about 12 to about 100 nucleotides may be used as primers to, for example, amplify all or part of an IBV S1 gene or modify an IBV S1 gene by site-specific mutagenesis. Fragments of about 10 to about 30 nucleic acids can be used, for example, in single stranded forms, double stranded forms, short hairpin RNAs, microRNAs or small interfering RNAs to alter the expression of the an IBV S1 gene by RNA interference or other DICER-mediated mechanisms. Fragments of about 20 to about 1000 nucleotides can be used, for example, in a variety of blot-based assays, including dot blots, northern blots, southern blots, and in situ hybridization assays.

Also included in the present invention are complements of the polynucleotides described herein. As used herein, "complement" and "complementary" refer to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in a polynucleotide base pairs with a nucleotide sequence in a second polynucleotide. For instance, 5'-ATGC and 5'-GCAT are complementary. Typically two polynucleotides are complementary if they hybridize under the standard conditions referred to herein.

The present invention includes polynucleotide sequences having a substitution of one, two, three, four, five, six, seven, eight, nine, ten, or more nucleotides. The present invention also includes the polynucleotide sequences described herein in which codon usage has been adapted to optimize expression in a given host cell. For example, codon usage may be adapted to optimize for expression in host cells including, but not limited to, baculovirus, yeast, E. coli, poultry, or human cells. Such adaptation can be carried out by techniques know in the art.

The present invention provides a recombinant vector containing one or more of the nucleotide sequences described herein. Such a recombinant vector may also include other sequences such as expression control sequences, markers, amplifying genes, signal sequences, promoters, and the like, as is known in the art. Useful vectors for this purpose are plasmids, and viruses such as baculoviruses, paramyxovirus, coronavirus, herpes virus (for example, herpes virus of turkeys (HVT)) and pox viruses, for example, fowl pox virus, and the like. Such a vector may be an expression vector selected for expression in vitro or in vivo or expression in prokaryotic cells or eukaryotic cells. The nucleic acids of the present invention may be used to produce constructs that express antigens. Such antigens may be utilized, for example, to produce antibodies, which may be used for identifying field or laboratory isolates of the present invention.

The present invention also includes host cells transformed with a polynucleotide sequence described herein and host cells transformed with a recombinant vector described herein. The host cell may be, for example, a eukaryotic or a prokaryotic host cell. Suitable examples are E. coli, insect cell lines such as Sf-9, chicken embryo fibroblast (CEF) cells, chicken embryo kidney (CEK) cells, African green monkey Vero cells and the like.

The present invention includes an S1 polypeptide of a ArkGA isolate as described herein, including, for example, a S1 polypeptide with an amino acid sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the amino acid sequence SEQ ID NO:2. In some embodiments, the S1 polypeptide includes one or more differences form a naturally occurring viral isolate. In some embodiments, the present invention includes a S1 polypeptide with an amino acid sequence that includes an asparagine residue at amino acid position 117 and/or a histidine residue at amino acid position 386. In some embodiments, the present invention includes an S1 polypeptide including the amino acid sequence SEQ ID NO:2.

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

The present invention includes polypeptides having the amino acid sequence SEQ ID NO:2, and truncations and fragments thereof. Truncations include, but are not limited to, amino acid sequences in which one, two, three, four, five, six, or more amino acids are removed from the amino terminus of the amino acid sequence and/or one, two, three, four, five, six, or more amino acids are removed from the carboxy terminus of the amino acid sequence. Fragments include, but are not limited to, for example, fragments having about 5, about 10, about 15, about 20, about 25, about 50, about 75, about 100, about 150, about 200, about 250, about 300, about 350, about 400, about 450, about 500, about 550, about 600, about 650, and about 700 consecutive amino acid residues of the sequence. Fragments also include, for example, fragments of a size range of any combination of the above fragment sizes. Fragments include, but are not limited to, for example, fragments having at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, and at least 700 consecutive amino acid residues.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from the amino acid sequence SEQ ID NO:2. Such amino acid changes include, but are not limited to, conservative amino acid changes. As used herein, the term "conservative substitution" refers to the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

As used herein, "structural similarity" refers to the identity between two polypeptides. Structural similarity is generally determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (*FEMS Microbiol Lett;* 174; 247-250, 1999) and available on the world wide web at ncbi.nlm.nih.gov/BLAST/. In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

The present invention includes antibodies that bind to an attenuated isolate of the Arkansas serotype of IBV as described herein and/or a S1 polypeptide, as described herein, and various antibody fragments, also referred to as antigen binding fragments, which include only a portion of an intact antibody, generally including an antigen binding site of the intact antibody and thus retaining the ability to bind antigen.

In some embodiments, while binding to an amino acid sequence of an S1 polypeptide as described herein, or a fragment thereof, such an antibody may not bind to a previously known IBV. Such a previously known isolates of IBV may include, for example, HN99, JAAS/04, N1/62, CA/557/03, CAV/CAV1686/95, CA/CA12495/98, CAV/CAV9437/95, Ark, Ark/ArkDPI/81, C2NDV, CU84074, CAV/CAV56b/91, CA/CA12495/98, Ark/Ark99/73, PP14/PP14/93, CAL99/CA1535/99, CAL99/NE15172/95, Holte/Holte/54, JMK/JMK/64, Gray/Gray/60, SE17/SE17/93, Iowa/Iowa609/56, B/D207/84, B/UK167/84, B/UK142/86, E/D3896/84, CAV/CA1737/04, DMV/5642/06, QX/IBVQX/99, 793B/4-91/91, Mass/H52, Mass/H120, Mass/Mass41/41, Mass/Beaudette, Conn/Conn46/51, FL/FL18288/71, DE/DE072/92, GA98/CWL470/98, GAD-utch/D1466/81, any of the GA07 or GA08 isolates described in WO 2009/143332 and U.S. Pat. No. 8,679,504.

Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Antibodies include, but are not limited to, polyclonal antibodies and monoclonal antibodies. The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

Monoclonal antibodies of the present invention can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention includes isolated viruses, polypeptides, polynucleotides, and antibodies. As used herein, "isolated" refers to material removed from its original environment (e.g., the natural environment if it is naturally occurring), and thus is altered "by the hand of man" from its natural state.

Viruses, polypeptides, polynucleotides, antibodies, and compositions thereof of the present invention may be stored until use in any of a variety of forms. For example, such materials, including, but not limited to, attenuated viral material, may be lyophilized and may be rehydrated for use. In another embodiment, materials may be frozen.

The present invention includes compositions of an attenuated isolate of the Arkansas serotype of IBV, a polynucleotide sequence, a vector, a cell, a polypeptide, or an antibody as described herein.

The viruses, polypeptides, polynucleotides, vectors, host cells, and compositions of the present invention may be administered to poultry or other animals to elicit an immune response to IBV virus and/or an IBV S1 polypeptide of the Arkansas serotype. The immune response may or may not confer protective immunity. Such an immune response may result in a reduction or mitigation of the symptoms of future IBV infection, for example, symptoms of an infection by an IBV virus of the Arkansas serotype. Such an immune response may prevent a future IBV infection in poultry, for example, preventing infection by an IBV virus of the Arkansas serotype. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein.

Vaccination for IBV is common for most commercial chickens. The vaccines are usually modified-live virus vaccines delivered through mass aerosol applications. The serotypes used in vaccination are often selected based on what serotypes the birds may be exposed to in the field. There is very little cross-protection between different serotypes of IBV. Accordingly, the present invention provides immunological materials that when administered do not result in significant clinical signs or lesions indicative of IBV disease. The present invention also provides immunological materials of low virulence, immunological materials with no increase in virulence when back passaged, and/or immunological materials that prevent infection with virulent wild type strains of IBV, including virulent wild type strains of the Arkansas serotype.

The viruses, polypeptides, polynucleotides, vectors, host cells, and compositions of the present invention may be administered to poultry or other animals as vaccines that reduce the susceptibility to disease induced by IBV. With such administration, the materials do not result in significant clinical signs or lesions indicative of IBV infection. Such animals may demonstrate circulating antibodies to IBV and/or reduced symptoms of IBV. Such compositions of matter may serve as vaccines that protect the birds from disease induced by IBV. In some embodiments, such compositions of matter may serve as vaccines that protect the birds from disease induced by the Arkansas serotype of IBV.

Compositions and vaccines of the present invention may include, for example, water or culture medium. Such compositions and vaccines may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate, and gentamicin. Diluents include, but are not limited to, water, aqueous buffer (such as buffered saline), alcohols, and polyols (such as glycerol).

Compositions of matter of the present invention may be substantially pure. As used herein, "substantially pure" will mean material essentially free of any similar macromolecules or other biological entities that would normally be found with it in nature. In some embodiments, the organisms used in such formulations are live. In some embodiments, the organisms, compositions, or vaccines may be lyophilized.

Immunogenic compositions and vaccines of the present invention may be administered to birds of any of a variety of avian species that are susceptible to IBV infection, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants.

"Poultry" is intended to embrace any breed of chicken, pheasant, emu, ostrich and other type of bird that is susceptible to infection by IBV. Chickens include, but are not limited to, hens, roosters, broilers, roasters, layers, breeders, the offspring of breeder hens, and layers. In some embodiments, the compositions of matter and methods of the present invention also apply to animals other than poultry that are susceptible to infection with IBV. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of an IBV infection, including, but not limited to, any of those described herein.

Compositions and vaccines of the present invention may be formulated for delivery by any of a variety of routes known in the veterinary arts, such as for example, mucosal, intranasal, intraocular, or oral administration. Compositions and vaccines of the present invention may be formulated for delivery to the respiratory mucosa and may be administered such that it is immediately or eventually brought into contact with the bird's respiratory mucosal membranes. Compositions and vaccines of the present invention may be formulated for delivery by any of a variety of modes known in the veterinary arts, such as for example, spraying or aerolizing.

An immunogenic composition or vaccine of the present invention may be administered by any suitable known method of inoculating birds including, but not limited to, nasally, ophthalmically, by eye drop, by injection, in drinking water, in the feed, by exposure, in ovo, maternally, and the like.

The immunogenic composition or vaccine may be administered by mass administration techniques such as by placing the vaccine in drinking water or by spraying the animals' environment. A composition may be administered by spraying an individual or the flock with a solution, such aerosol delivery may involve the administration of the composition incorporated in small liquid particles. Such spray-type particles may have a droplet size ranging from between about 10 to about 100 microns, more preferably, a droplet size from between about <1 to about 50 microns. For the generation of the small particles, conventional spray-apparatus and aerosol generators may be used, such as the commercially available spray generators for knapsack spray, hatchery spray and atomist spray. Administration through drinking water may be carried out using conventional apparatus. When administered by injection, the immunogenic composition or vaccine may be administered parenterally. Parenteral administration includes, for example, administration by intravenous, subcutaneous, intramuscular, or intraperitoneal injection.

A composition or vaccine of the present invention may be administered to birds before or after hatching. Birds may receive such a composition of vaccine at any of a variety of ages. With delivery after hatching, materials may be delivered, for example, about one week after hatching, about two weeks after hatching, about three weeks after hatching, about four weeks after hatching, about five weeks after hatching, about six weeks after hatching, or any range thereof. For in ovo administration, materials may be delivered about seventeen days of incubation, about eighteen days of incubation, about nineteen days of incubation, about twenty days of incubation, and any range thereof.

An immunogenic composition or vaccine of the present invention may further include one or more immunogens derived from other pathogens infectious to poultry. Such immunogens may be derived from, for example, Marek's disease virus (MDV), other serotypes of infectious bronchitis virus (IBV), including, but not limited to, any of those described herein, Newcastle disease virus (NDV), egg drop syndrome (EDS) virus, turkey rhinotracheitis virus (TRTV), poxvirus, or reovirus.

The viruses, polypeptides, polynucleotides, vectors, host cells, and antibodies of the present invention may be utilized in any of the commonly used methods for IBV detection, such as, for example, hemagglutination (HA) (Lashgari and Newman, 1984, *Avian Dis;* 28:435-443), hemagglutination inhibition (King and Hopkins, 1983, *Avian Dis;* 27:100-112), AGPT (Lohr, 1980, *Avian Dis;* 24:463-467; and Lohr 1981, *Avian Dis;* 25:1058-1064), and RT-PCR (Kwon et al., 1993, *Avian Dis;* 37:194-202).

The present invention also includes methods for the detection of IBV isolates, the identification of IBV serotypes, the detection of IBV genotypes, and the detection of antibodies to IBV, including the detection of an IBV infection or the detection of previous exposure of an animal to IBV. In some aspects, the IBV isolate is of the Arkansas serotype and/or genotype, for example, as defined by the Ark99 or the p60 ArkGA isolate described herein. Such a method may employ determining that an antisera sample includes antibodies that specifically bind to a polypeptide of the present invention. Such a method may employ detecting the hybridization of a polynucleotide of the present invention to a sample, preferably under high stringency conditions. Such a method may employ producing a polymerase chain reaction (PCR) amplification, where the resultant amplicon demonstrates a sequence similar to a nucleotide sequence of the present invention. Such a method may employ producing a PCR amplification utilizing a primer pair described herein. The polypeptides, polynucleotides, and/or antibodies may be labeled with one or more of the detectable markers known to the skilled artisan. In some aspects, the polypeptides, polynucleotides, and/or antibodies may be bound to a solid substrate.

Antibodies may be detected by any of a variety of methods, including, but not limited to, the methods described herein and any suitable method available to the skilled artisan. Immunoassays that can be used include, but are not limited to, competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art.

In some embodiments, primers, including, but not limited to any of those described herein, may be used in PCR to amplify the nucleotide sequence encoding a S1 glycoprotein from a sample, and the products compared via sequence analysis or hybridization, to nucleic acid sequence described herein, to identify an IBV virus of the Arkansas serotype.

The present invention includes a method of detecting IBV in a sample, the method including identifying in the sample a nucleotide sequence as described herein. For example, the present invention includes a method of detecting IBV in a sample, the method including identifying in the sample a nucleotide sequence having at least 90%, at least 91%, at least 92%, at least 93%, at least 94%, at least 95%, at least 96%, at least 97%, at least 98%, or at least 99% sequence identity to the nucleotide sequence SEQ ID NO:1. In some aspects, the method includes identifying in the sample a nucleotide sequence having the nucleotide sequence SEQ ID NO:1.

The present invention includes a method of detecting IBV in a sample, the method including identifying in the sample an S1 amino acid sequence as described herein. In some embodiments, the present invention includes a method of detecting IBV in a sample, the method including identifying in the sample an amino acid sequence having at least 90%, at least 91%, at least 92%, at least 93%, at least 94%, at least 95%, at least 96%, at least 97%, at least 98%, or at least 99% sequence identity to the amino acid sequence SEQ ID NO:2. In some aspects, the method includes identifying in the sample an amino acid sequence having the amino acid sequence SEQ ID NO:2.

The present invention includes kits employing one or more of the viruses, polypeptides, polynucleotides, and/or antibodies described herein. Such kits may provide for the administration of a polypeptide or polynucleotide of the present invention to an animal in order to elicit an immune response. Such kits may provide for the detection of a polypeptide, antibody or polynucleotide, for example, for the detection of IBV infection or exposure to an IBV agent in an animal. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

Any of the diagnostic methods of the present invention may include the additional step of providing a report or print out of the results. The sample may be any sample in which IBV antibodies, viruses, antigens, or nucleotides are present, for example, a blood, serum or tissue sample. Such methods and kits may also provide for the detection of infectious IBV agents in environmental samples.

While the invention has been described in connection with specific embodiments, it will be understood that it is capable of further modifications and the appended. Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising.

The present invention is illustrated by the following examples. It is to be understood that the particular examples, materials, amounts, and procedures are to be interpreted broadly in accordance with the scope and spirit of the invention as set forth herein.

EXAMPLES

Example 1

A New Arkansas Serotype Infectious Bronchitis Virus Vaccine

Almost all commercial poultry are vaccinated against avian coronavirus infectious bronchitis virus (IBV) using live attenuated vaccines applied by spray in the hatchery. Although many different types of IBV vaccines are used successfully, the Arkansas Delmarva Poultry Industry (ArkDPI) serotype vaccine, when applied by spray, did not infect and replicate predictably like other IBV vaccine serotypes. Because efforts to improve the efficacy of ArkDPI vaccines applied by spray have been unsuccessful, the Arkansas 99 (Ark99) vaccine strain, a previously used but relatively reactive IBV vaccine, was investigated for use in a hatchery spray cabinet. The Ark99 vaccine was further attenuated by passage in embryonated eggs to reduce reactivity. During the attenuation process, egg passages 1, 20, 40, and 60 (designated ArkGA after P1) were sequenced using complete genome Illumina sequencing to examine the genome changes occurring. Through passaging, the ArkGA vaccine accumulated single nucleotide polymorphisms (SNPs) in regions of the genome associated with viral replication, pathogenicity, and cell tropism, and the genetic population became more stable and homologous. Subsequent egg passages were also examined for infection, replication and attenuation in one-day old broiler chicks. ArkGA P1, P20, and P40 were deemed too reactive and not suitable as a vaccine candidate, but ArkGA P60 appeared to be safe and efficacious when given by spray to broiler chicks, with little or no clinical signs observed. The vaccine also induced good protection from clinical signs and ciliostasis and significantly reduced viral load following homologous challenge, determined by quantitative real-time reverse-transcriptase polymerase chain reaction (qRT-PCR) and virus isolation in embryos, compared to non-vaccinated controls. These results indicate that the ArkGA P60 vaccine is safe for spray vaccination of broiler chicks and induces suitable protection against challenge with homologous Ark-type virus.

Because of its prevalence and infectivity, nearly all commercial poultry in the U.S. are vaccinated against IBV in a serotype-specific manner (Cavanagh, 2007, *Vet Res;* 38:281-2974 and Jordan, 2017, *Vet Micro;* 206:137-143. Of the vaccines used in the U.S., the Arkansas Delmarva Poultry Industry (ArkDPI) serotype vaccine has been shown to be highly variable in its protective ability, and is frequently isolated from vaccinated chicks (Jackwood et al., 2005, *Avian Dis;* 49:614-618, Ndegwa et al., 2014, *Avian Dis;* 58:102-110, and Toro et al., 2006, *Avian Pathol;* 35:455-464). It has been shown that the ArkDPI vaccine has an atypical infection and replication pattern when mass applied by spray, and previous data from our laboratory suggests that levels of vaccine virus infection post-vaccination only reach 15-25% (Jackwood, et al., 2009, *Avian Dis;* 53:175-183). Chickens do not develop adequate immunity after ArkDPI vaccination. While ArkDPI is the only commercially available Ark-type IBV vaccine today, it is not the only Ark-type IBV vaccine ever produced. The Arkansas 99 (Ark99) strain was the first Ark-type virus to be attenuated for use as a vaccine. When originally mass applied in the field, it caused a severe vaccine reaction in young broilers, and was therefore discontinued when ArkDPI was developed (Fields, 1973, *Avian Dis;* 17:659-661 and Johnson et al., 1973, *Avian Dis;* 17:518-523.

This example, confirmed the reactivity of the original Ark99 vaccine when administered to 1-day old broilers by spray, followed by evaluation of infection, replication, and protection from challenge of further embryo passages. We also investigated the mechanisms of attenuation of this vaccine during the subsequent embryo passages. This Example led to development of a new, further attenuated vaccine designated Arkansas Georgia (ArkGA) vaccine.

Materials and Methods

Vaccine and challenge viruses. Ark99 vaccine is no longer in production and a USDA license is not maintained by any vaccine manufacturer, so an archived reference sample of live Ark99 vaccine was obtained from a commercial source. This reference sample was passaged once in 9-to-11 days of incubation specific-pathogen free (SPF) chicken embryos as described below. The University of Georgia egg-passaged virus, now designated ArkGA, was then used for further experimentation. Different egg passages, beginning at egg passage 1 (P1) and going to P60, were used in this study for consecutive experiments. A pathogenic Arkansas serotype challenge virus from our laboratory was also used in this study.

Embryonated chicken eggs and chickens. Specific-pathogen free (SPF) embryonated chicken eggs were purchased from Charles River Laboratories (North Franklin, Conn.) and incubated to 9-to-11 days of development for virus passage, titration, and isolation experiments. Commercial non-vaccinated broiler chickens were used in the vaccination experiments as described below.

Virus attenuation. ArkGA was passaged 60 times by inoculating 9-to-11-day-old embryonated chicken eggs via the chorioallantoic sac (CAS) route (Dufour-Zavala, "A laboratory manual for the isolation, identification and characterization of avian pathogens," 5th ed. ed. American Association of Avian Pathologists, Jacksonville, Fl. 2008. Inoculated eggs were incubated at 37° C. for 48 hours, at which point the chorioallantoic fluid was collected for subsequent passage. At every 20$^{th}$ passage the S1 portion of the spike gene was sequenced to detect any mutations.

Virus titration. Viruses were titrated at different egg passage levels using the following protocol: 10-fold serial dilutions of the virus were made in sterile deionized water and each dilution was inoculated into five 10-day-old embryonated SPF chicken eggs (0.1 ml/egg). Inoculated eggs were incubated at 37° C. for 7-days and embryos were examined for IBV-specific lesions. Embryo mortality within 24-hours post-inoculation was considered nonspecific and not included in virus titer calculations. Virus titers were calculated by the method of Reed and Muench (Reed and Muench, 1938, *American Journal of Hygiene* 27:493-497) and expressed as the 50% embryo infectious dose (EID$_{50}$).

Experiment 1 (Safety testing of ArkGA). Thirty 1-day-old SPF chicks were vaccinated via the oculonasal route with a 10× dose of ArkGA P1 vaccine and placed into Horsfal isolation units. Twelve chicks remained non-vaccinated as controls. At 5, 7, and 10 days post-vaccination, all chicks were swabbed in the choanal cleft, and swabs were placed in deionized water and stored at −80° C. until used for qRT-PCR quantification. In addition, 5 chicks at each swab time point were euthanized and tracheas were collected for ciliostasis scoring via the method described above. Two non-vaccinated chicks were also euthanized at each time point and ciliostasis was evaluated for comparison. At each time point, clinical signs, such as snicks and rales, were recorded.

Experiment 2 (Evaluation of infection and replication of ArkGA P1 and protection from challenge). One hundred one-day-old broiler chicks were spray vaccinated with the ArkGA P1 vaccine candidate in a 7 ml volume and placed in a colony type housing unit on fresh litter. Ten additional non-vaccinated chicks were placed in isolators as controls. At 7, 10, 14, 17, 21, 24, and 28 days post-vaccination, all vaccinated chicks were swabbed in the choanal cleft for qRT-PCR analysis of viral load as previously described. Clinical signs corresponding to vaccine reactions were also recorded on those days. On day 30 post-vaccination, 20 vaccinated and 5 non-vaccinated chickens were challenged with pathogenic Ark-type IBV, while an additional 5 vaccinated and 5 non-vaccinated chickens were held as non-challenged controls. Five days post-challenge, clinical signs were recorded and all chickens were swabbed and euthanized for necropsy. Tracheas were collected at necropsy for ciliostasis scoring.

Experiment 3 (Evaluation of infection and replication of ArkGA P20, ArkGA P40, and ArkGA P60 vaccine candidates and protection from challenge). Experiment 3 was carried out in the same manner as Experiment 2 for ArkGA P20, ArkGA P40, and ArkGA P60 vaccine candidates.

Experiment 3 (Trial 1). A severe vaccine reaction in broiler chickens caused by the ArkGA P1 vaccine candidate necessitated further virus attenuation by 19 additional embryonated egg passages, yielding the ArkGA P20 vaccine candidate. One hundred one-day-old broiler chicks were spray vaccinated with the ArkGA P1 vaccine candidate in an 18 ml volume and placed in a colony type housing unit on fresh litter. Ten additional non-vaccinated chicks were placed in isolators as controls. Swabs were taken at 3, 5, 7, 10, and 14 days post-vaccination to assess viral load and vaccine coverage in chicks, and clinical signs were recorded.

Experiment 3 (Trial 2). The ArkGA P20 vaccine candidate was passaged an additional 20 times in embryonated eggs to produce the ArkGA P40 vaccine candidate and another vaccination trial was conducted as described in Trial 1.

Experiment 3 (Trial 3). The ArkGA P40 vaccine candidate was passaged an additional 20 times in embryonated eggs to further attenuate the virus, producing ArkGA P60. One hundred one-day-old broiler chicks were spray vaccinated with the ArkGA P60 vaccine candidate in an 18 ml volume and placed in a colony type housing unit on fresh litter. Ten additional non-vaccinated chicks were placed in isolators as controls. At 3, 5, 7, 10, 14, 17, 21, 24, and 28 days post-vaccination, all vaccinated chicks were swabbed in the choanal cleft for qRT-PCR analysis of viral load as previously described. Clinical signs corresponding to vaccine reactions were also recorded on those days. On day 30 post-vaccination, 20 vaccinated and 5 non-vaccinated chickens were challenged with pathogenic Ark-type IBV, while an additional 5 vaccinated and 5 non-vaccinated chickens were held non-challenged as controls. Five days post-challenge, clinical signs were recorded and all chickens were swabbed and euthanized for necropsy. Tracheas were collected at necropsy for ciliostasis scoring.

Virus detection using quantitative real-time RT-PCR. Viral RNA was extracted from 50 µl of choanal swab fluid using the MagMAX-96 RNA Isolation Kit (Ambion Inc., Austin Tex.) on a KingFisher Flex magnetic particle processor (Thermo Scientific, Waltham, Mass.) per the manufacturer's protocol. Quantitative real-time RT-PCR (qRT-PCR) was conducted using an Applied Biosystems 7500 Fast Real-Time PCR System (Life Technologies, Carlsbad, Calif.) and the AGPATH-ID™ One-Step RT-PCR kit (Ambion Inc.) per the manufacturer's recommendations. Primers and probe for the qRT-PCR were previously published (Callison et al., 2006, *J Virol Meth;* 138:60-65 and consist of a forward primer IBV5'GU391 (5'-GCT TTT GAG CCT AGC GTT-3') (SEQ ID NO: 3), a reverse primer IBV5'GL533 (5'-GCC ATG TTG TCA CTG TCT ATT G-3') (SEQ ID NO: 4) and a TAQMAN® dual-labeled probe IBV5'G probe (5'-FAM-CAC CAC CAG AAC CTG TCA CCT C-BHQ1-3') (SEQ ID NO: 5). Cycle-threshold (CT) values above the limit of detection for the assay were considered negative (Roh et al., 2014, *Avian Dis;* 58:398-403. All positive samples were used to determine the total percent positive for each group.

Ciliostasis scoring. The ciliostasis test was conducted by examining five rings approximately 1 mm thick cut from each chicken trachea representing the proximal, middle and distal portion. Cilia activity was observed with an inverted microscope (Olympus, Center Valley, Pa.) and scored as: 0, all cilia beating; 1, 75% of cilia beating; 2, 50% of cilia beating; 3, 25% of cilia beating; 4, no cilia beating. Each ring was scored by 3 individuals and the average total score for each trachea was calculated using the formula: 100−[(total of the individual scores for the group)/(the number of individuals in the group×20)×100]. An individual bird is considered protected if the score is greater than 50 (Cook et al., 1976, *Arch. Virol;* 50:109-118.

Challenge virus detection in embryonated eggs. Routine virus isolation techniques were used for detection of IBV challenge virus in 9-to-11 days of incubation embryonated SPF chicken eggs. Briefly, 2 ml of ice-cold phosphate-buffered saline (PBS) were added to the choanal swab fluid to match the stipulations of the U.S. Code of Federal Regulations, title IX (9-CFR) (Service, "P. H. I. Title 9, code of federal regulations, standard requirements for IBV vaccines," In USDA Animal and Plant Health Inspection Service, ed., Washington, D.C. 2011. PBS from the swabs was filter sterilized and 0.2 ml of each sample were inoculated into the chorioallantoic sac of 6 embryonated chicken eggs. Eggs were candled daily (24-72 hour deaths were discarded) for 7 days and the number of deaths and embryo lesions consistent with IBV infection was recorded.

Figure 6A:
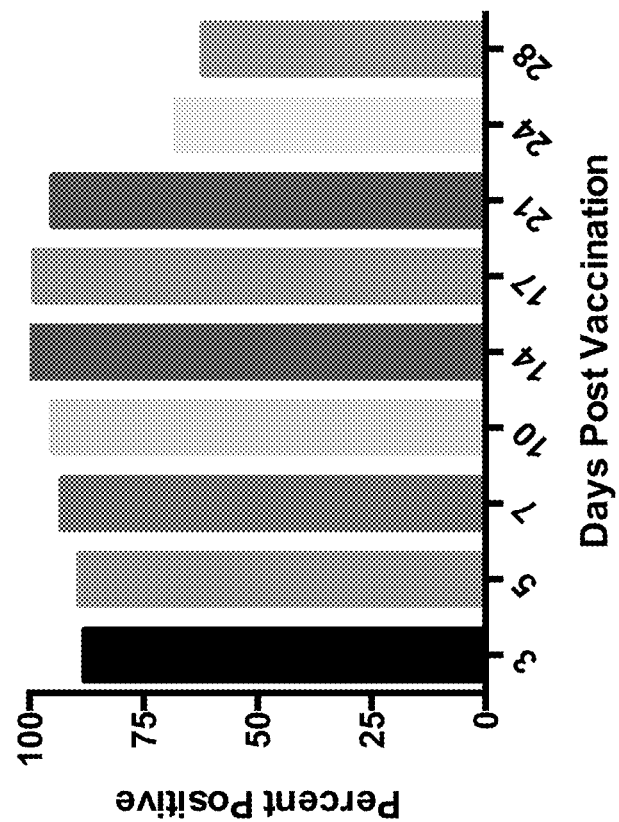
FIGS. 6A and 6B. Viral loads in chickens and vaccine coverage post-vaccination with ArkGA P60 of Experiment 3, Trial 3. Ct=cycle threshold.
Figure 6B:
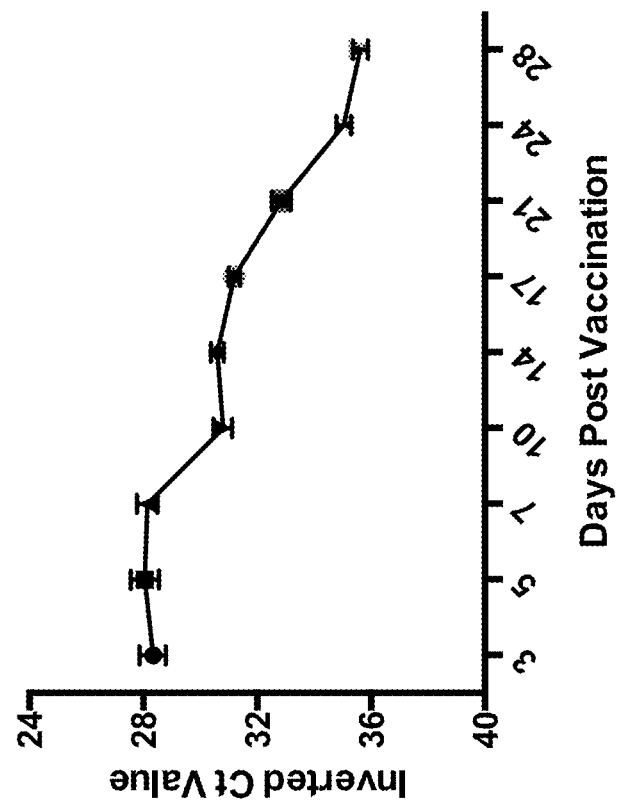

Sequence analysis of the S1 gene. The S1 portion of the ArkGA spike gene was sequenced at passages 1, 20, 40, and 60. Viral RNA was purified using the Zymo Direct-zol RNA miniprep kit (Zymo Research, Irvine Calif.). S1 gene sequences were amplified by RT-PCR using the Titan One-Step RT-PCR system (Roche Diagnostics, Indianapolis, Ind.) and previously published primers: NEWS1OLIGO5' (Jackwood et al., 1997, *Avian Dis;* 41(1):105-110) and Degenerate3' (Lee et al., 2000, *Avian Dis;* 44(3):650-654. RT-PCR reactions were analyzed on a 1% w/v agarose gel and bands of the correct size were excised and DNA was purified from the gel fragment using the GeneJET Gel Extraction Kit (Thermo Scientific, Waltham, Mass.). Sequencing reactions were performed by the Georgia Genomics Facility, University of Georgia, Athens, Ga. The S1 sequences were assembled and compared using the DNAStar suite of programs (DNAStar, Madison Wis.).

Post-vaccination choanal cleft palate swab analysis. For ArkGA P1, ArkGA P20, ArkGA P40, and ArkGA P60 vaccination trials, viral RNA from 5 choanal cleft palate swabs was purified from days 7, 10, and 14 post-vaccination for sequencing of the S1 region of the genome as described previously. The S1 amino acid sequences of viral RNA isolated from vaccinated chickens was compared to the S1 sequences of the vaccine virus for P1, P20, P40, and P60 to detect any mutations that occurred after viral replication in chicken tissues.

Genome Sequencing. In addition to sequencing of the S1 region of the viral genome, complete genome sequencing was performed on ArkGA P1, ArkGA P20, ArkGA P40, and ArkGA P60 to detect changes occurring within the viral genome during attenuation and for comparison to pathogenic and vaccine strains of ArkDPI. Virus stock was filtered with a 0.2 μm syringe filter. Viral RNA was extracted from samples using the Direct-Zol RNA MiniPrep Kit (Zymo Research) and treated with DNase I (New England Biolabs).

Complementary DNA (cDNA) was synthesized using SuperScript IV (Invitrogen/Thermo Scientific). Double stranded cDNA (dsDNA) was generated from cDNA templates using Second Strand cDNA Synthesis Kit (Applied Biological Materials Inc.). Complete genome sequencing was conducted using the Nextera XT DNA Sample Preparation Kit (Illumina) and MiSeq sequencer (Illumina) according to manufacturer's instructions. De Novo and directed assembly of genome sequences were carried out using the MIRA3 sequence assembler and Geneious r8 program (available on the worldwide web at geneious.com). Non-synonymous substitutions in the assembled sequence reads were compared to consensus sequence at 5% of minimum variant frequency using Geneious r8 program.

Animal care. All experiments in this research were conducted in accordance with animal care and use protocols approved by the University of Georgia IACUC committee.

Results

Experiment 1. Infection and replication characteristics of the ArkGA P1 vaccine candidate were typical of other IBV vaccine types following eyedrop vaccination of SPF chickens (Table 1). All vaccinated chickens swabbed were positive for vaccine virus by 5-days post-vaccination, though viral load as indicated by Ct values was not as high as expected. By 10-days post-vaccination, 19/20 vaccinated chickens were positive for ArkGA and the viral load had decreased, indicating that the chickens were beginning to clear the vaccine. No non-vaccinated chickens were positive for ArkGA at any time during this trial. Ciliostasis scores differed between vaccinated and non-vaccinated chickens at all time points (FIG. 1), though both groups passed the ciliostasis test. On day 10 post-vaccination, when the largest difference in ciliostasis scores between vaccinated and non-vaccinated chickens (53 vs 89) was seen, tracheal rales were also heard in one chicken in the vaccinated group.

Experiment 2. One hundred commercial broiler chickens were vaccinated with the ArkGA P1 vaccine candidate in a 7 ml volume by spray using a commercial hatchery vaccine spray cabinet at a dose of $1\times10^{3.5}$ $EID_{50}$ per bird. All chickens were swabbed at 7, 10, 14, 17, 21, 24, and 28-days post-vaccination to assess viral load and vaccine infection rate (coverage), and the data are presented in FIG. 2. Viral load in chickens was high by day 7 post-vaccination, and remained constant until 14-days post-vaccination at which point it began to decrease (FIG. 2A). ArkGA P1 vaccine candidate coverage was 100% by day 7 post-vaccination, and remained constant throughout the course of the experiment (FIG. 2B). Clinical signs were also recorded at these time points and tracheal rales were observed in 60% of the chicks vaccinated with ArkGA P1 vaccine candidate at 10 days post-vaccination, which is consistent with previous reports for Ark99.

At 30 days post-vaccination, chickens were challenged with $1\times10^{3.4}$ $EID_{50}$ (50% embryo infectious dose) of pathogenic Arkansas serotype virus in a 0.1 ml eyedrop application and the data collected at five days post-challenge is shown in FIG. 3. All groups showed significantly less clinical signs than the non-vaccinated and challenged group (FIG. 3A), and all groups passed the ciliostasis test except for the non-vaccinated and challenged group (FIG. 3B), as expected. Relative viral load was also significantly reduced in all groups when compared to the non-vaccinated and challenged group (FIG. 3C). Plotting the individual samples taken from each group shows that 4/20 chickens in the ArkGA P1 vaccinated and challenged group were positive by qRT-PCR. (FIG. 3D). Virus isolation was not performed for this trial.

Experiment 3. Experiment 3 encompasses three separate trials carried out in the same manner as Experiment 2 for ArkGA P20, P40, and P60 vaccine candidates, with the exception that vaccine was applied in an 18 ml total volume per 100 chicks and vaccination experiments for ArkGA P20 and P40 vaccine candidates were ended prior to challenge due to excessive clinical signs post-vaccination.

Experiment 3 (Trial 1). As seen before, for chicks vaccinated with ArkGA P20, viral load and vaccine coverage were typically high early post-vaccination (FIG. 4). However, thirty percent of chickens vaccinated with ArkGA P20 showed severe clinical signs (rales) on day 10 post-vaccination, which is reduced from the previous trial but still much higher than what would be accepted by the commercial poultry industry. For this reason, Trial 1 was ended at this point.

Experiment 3 (Trial 2). In chicks vaccinated with ArkGA P40, viral load and vaccine coverage were lower at days 3 and 5 post-vaccination than in Trial 1, but reached high levels by day 7 post-vaccination (FIG. 5). Clinical signs (rales) were reduced to 10% of chicks with tracheal rales at 10 days post-vaccination, which was less than Trial 1, but was still considered too pathogenic for a commercial poultry vaccine. For this reason, Trial 2 was ended at this point.

Experiment 3 (Trial 3). One hundred broiler chickens spray vaccinated with ArkGA P60 with a dose of $1 \times 10^{3.1}$ EID$_{50}$ per bird were swabbed on 3, 5, 7, 10, 14, 17, 21, 24, and 28-days post-vaccination, and viral load and vaccine coverage are shown in FIG. 6. Viral load in chicks was again high soon after vaccination, though coverage was lower than expected on days 3 and 5 post-vaccination. By 7 days post-vaccination, coverage had reach 93% and peaked at 100% on day 14 post-vaccination. By 21 days post-vaccination, chickens began to clear the vaccine virus, indicated by reduced viral load and coverage (FIG. 6). Only 3% of chicks vaccinated with ArkGA P60 showed clinical signs (snicks), which was deemed acceptable for an IBV vaccine, so the challenge portion of this trial was carried out to assess protection.

Figure 7A:
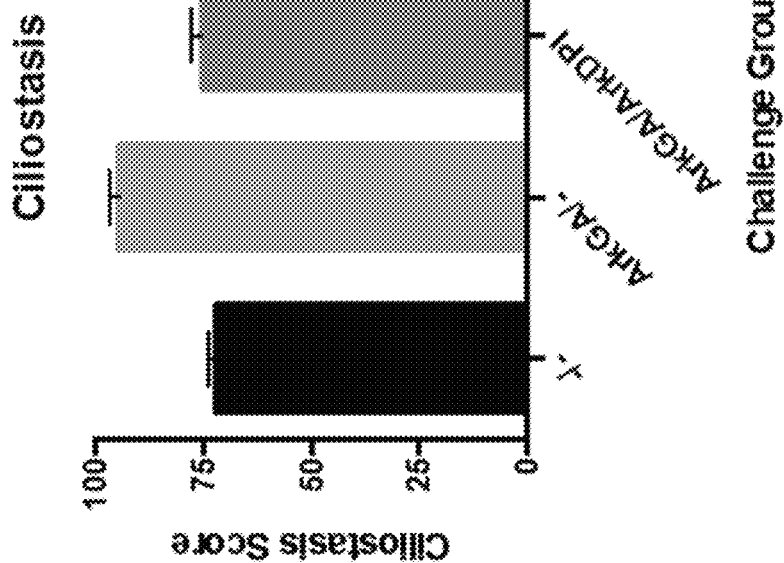
FIGS. 7A-7D. ArkGA P60 vaccinated and non-vaccinated clinical signs, ciliostasis scores, and viral loads in chickens post-challenge of Experiment 3, Trial 3.
Figure 7B:
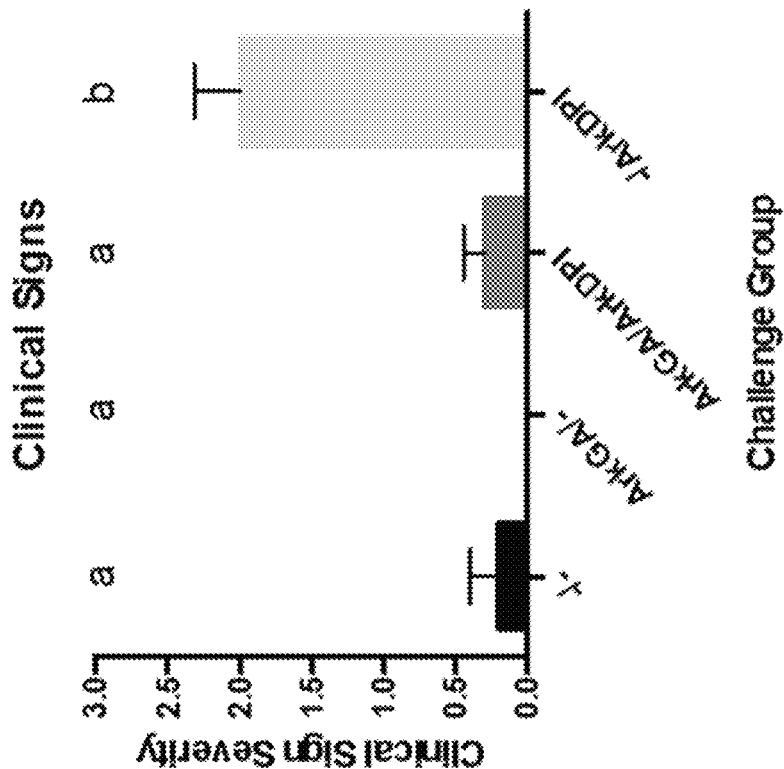

On day 30 post-vaccination, 20 ArkGA P60 vaccinated and 5 non-vaccinated chickens were challenged with $1 \times 10^{3.4}$ EID$_{50}$ of pathogenic Arkansas virus, and 5 vaccinated and 5 non-vaccinated chickens were kept non-challenged as controls. Five-days post-challenge, the birds were euthanized and a necropsy was performed, and the data are presented in FIG. 7. All groups showed significantly reduced clinical signs (FIG. 7A) and viral loads (FIG. 7C) compared to the non-vaccinated/challenged group, and all groups except the non-vaccinated/challenged group passed the ciliostasis test (FIG. 7B).

Figure 7D:
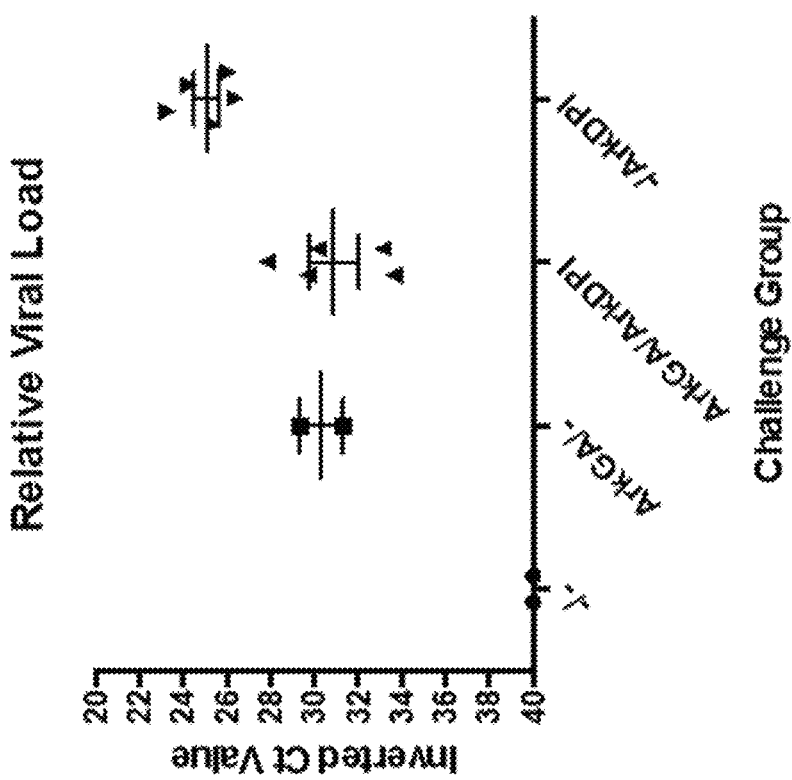
Figure 7C:
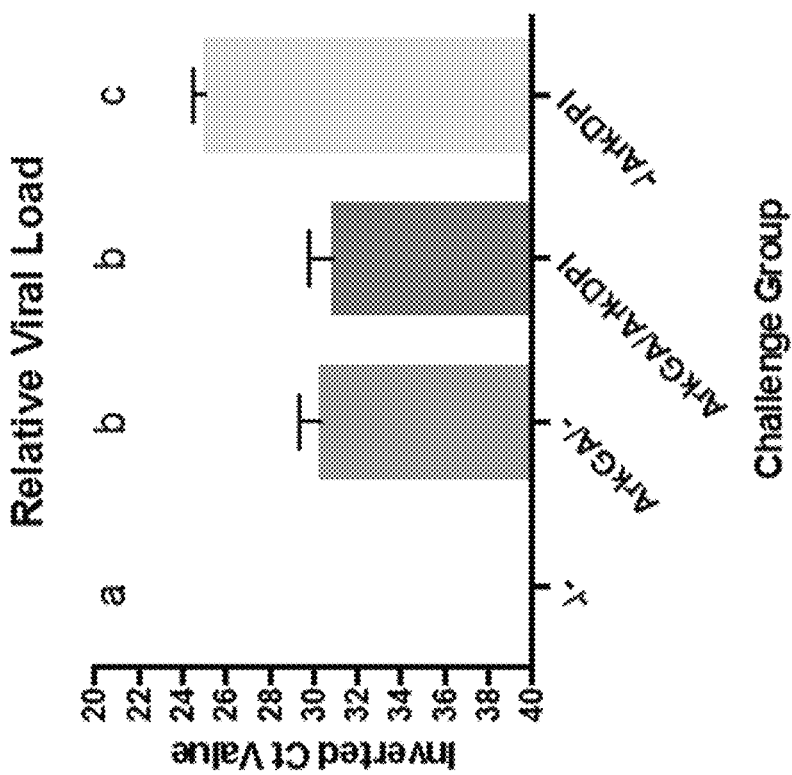

When analyzing the individual viral load values, 5/20 of the vaccinated and challenged birds were positive by qRT-PCR. It should also be noted that the ArkGA P60 vaccinated/non-challenged group had 2/5 chickens positive for virus (FIG. 7D).

Virus isolation post challenge was consistent with the results found by qRT-PCR (Table 2). All of the non-vaccinated and non-challenged group swabs were negative for virus isolation. In the vaccinated/non-challenged group, one of the swabs was found to be positive with an embryo death at 120-hours post-inoculation. All 5 of the other embryos in this set died by 72-hours post-inoculation however, indicating a possible bacterial contamination in that sample. In the vaccinated/challenged group, 3/19 of the swabs were found to be positive for ArkDPI. All embryos in the 20$^{th}$ swab sample died at 48 hours post-inoculation, so that sample could not be analyzed. All 5 of the non-vaccinated/challenged bird swabs were positive for IBV.

To ensure that virus isolation positives in challenged groups were indeed challenge virus and not residual vaccine, the spike gene of samples from both challenged groups was sequenced. In all instances, sequence matched the Arkansas challenge virus, indicating it was not residual vaccine. In the vaccinated/non-challenged group, no sequence could be obtained from qRT-PCR positive samples.

Sequence analysis of the S1 gene. A comparison of the S1 portion of the spike gene of ArkGA P1 vs ArkDPI reveals at least 20 differences in the amino acid sequence. Of note, ArkGA P1 spike sequence contains a histidine at position 43, which has been previously shown to significantly increase spike protein binding to chicken tracheal tissues, and an asparagine deletion at position 344, which has been shown to influence the ability of antibodies to recognize the protein (Leyson et al., 2016, *Virology*; 498:218-225).

The S1 portion of the ArkGA spike gene was sequenced at every twentieth passage during further attenuation to evaluate changes that may have occurred during the embryo adaptation/attenuation process. No amino acid changes were seen in passages 1, 20, and 40, but in passage 60 a serine to asparagine change at position 117 and an arginine to histidine change at position 385 were detected.

Analysis of the ArkGA P1, P20, P40, and P60 S1 sequence isolated from vaccinated birds. During the ArkGA P1, P20, P40, and P60 vaccination trials, swabs collected from 5 chickens on days 7, 10, and 14 post-vaccination were analyzed for S1 sequence comparison with the vaccine, and results are shown in Table 3. Included in Table 3 are amino acid positions in the S1 sequence that exhibited variation among the different ArkGA passages. All other amino acid positions remained consistent throughout passaging. No difference was seen between the ArkGA P1 vaccine virus and the virus re-isolated from vaccinated chickens. When analyzing P20 and P40, position 198 showed a changed from lysine to lysine/threonine in the swab virus, and a glycine to glycine/aspartic acid change was seen at position 200. An additional mutation was seen in P40 at position 130, where a serine was present in the vaccine and a serine or asparagine could be seen in the swab sequence. These mutations were not maintained in P60, however in this passage new mutations occurred in the vaccine sequence compared to previous passages. As noted previously, in the ArkGA P60 vaccine, at position 117 an asparagine was present where in all other passages there was a serine, and the same occurrence was seen at position 385 where a histidine was present in P60 vs an arginine in this location for all earlier passages. For both amino acid changes seen in the P60 vaccine sequence, the virus re-isolated from swab material showed a reversion to the sequence shown in the previous vaccine passages.

Figure 8:
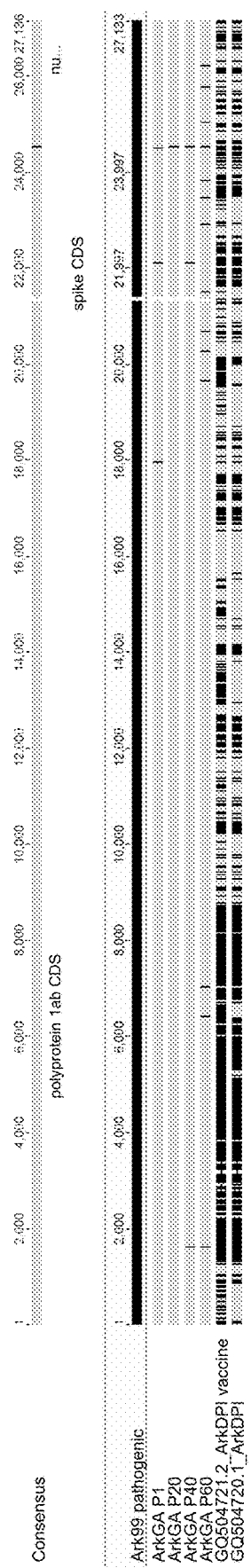
FIG. 8. Consensus sequences during attenuation of the ArkGA IBV vaccine candidate in comparison to Ark99 pathogenic field strain, ArkDPI pathogenic field strain, and ArkDPI vaccine genomes.

Whole genome sequencing of ArkGA P1, P20, P40, and P60. FIG. 8 shows the consensus sequences of ArkGA P1, P20, P40, and P60 as compared to the original pathogenic Ark99 virus and the ArkDPI vaccine and pathogenic viruses. In all passages, the ArkGA viral genome was highly different from the ArkDPI virus genome, though serotypically they are the same virus type. Over the 60 additional passages performed, the ArkGA vaccine accumulated 14 single nucleotide polymorphisms (SNPs) compared to the Ark99 pathogenic virus. When examining these SNPs, a SNP emerged in the leader sequence of the genome in ArkGA P40 and was maintained in P60. In addition, two SNPs emerged in the nsp3 protein gene region in ArkGA P60, and a large number of SNPs occurred in the spike protein gene.

In addition to comparing the consensus sequences of the ArkGA passages, whole genome sequencing was also used to evaluate the frequency of variant SNPs found in each passage. The number of variant SNPs in the Ark99 pathogenic virus was low, and the frequency was small (Table 4). As the virus was passaged in embryonated eggs, the number of variant SNPs increased to P60. Initially during passaging, the frequency of the variants increased (Tables 5-7), however a decrease in variant frequency was seen in ArkGA P60 (Table 8) as the population became more adapted to embryos.

TABLE 1

Experiment 1. ArkGA P1 vaccine candidate detection in SPF chickens by real-time PCR during safety testing.

| Group | Day 5 | Day 7 | Day 10 |
|---|---|---|---|
| Vaccinated | 30/30 | 25/25 | 19/20 |
| | (31.48 ± .39)$^A$ | (32.41 ± .49) | (34.90 ± .46) |
| Non-Vaccinated | 0/12 | 0/10 | 0/8 |

$^A$Number in parentheses represents average Ct value.

TABLE 2

Experiment 3, Trial 3. Pathogenic Ark-type challenge virus detection in embryonated eggs. Data are represented as the number embryos positive per total for classic IBV signs 7 days post inoculation.

| Group | Chicken | ArkDPI |
|---|---|---|
| Non-Vaccinated/Non-Challenged | 1 | 0/6[A] |
|  | 2 | 0/6 |
|  | 3 | 0/6 |
|  | 4 | 0/6 |
|  | 5 | 0/6 |
| Vaccinated/Non-Challenged | 6 | 0/5 |
|  | 7 | 0/6 |
|  | 8 | 0/6 |
|  | 9 | 0/6 |
|  | 10 | 1/1 |
| Vaccinated/Challenged | 11 | 0/6 |
|  | 12 | 0/4 |
|  | 13 | 0/5 |
|  | 14 | 0/6 |
|  | 15 | 0/6 |
|  | 16 | 0/6 |
|  | 17 | 0/4 |
|  | 18 | 0/6 |
|  | 19 | 0/4 |
|  | 20 | 0/5 |
|  | 21 | 0/4 |
|  | 22 | 1/6 |
|  | 23 | 0/6 |
|  | 24 | 0/3 |
|  | 25 | 3/6 |
|  | 26 | 0/5 |
|  | 27 | 1/6 |
|  | 28 | 0/3 |
|  | 29 | 0/6 |
|  | 30 | 0/6* |
| Non-Vaccinated/Challenged | 31 | 3/6 |
|  | 32 | 1/5 |
|  | 33 | 1/6 |
|  | 34 | 3/6 |
|  | 35 | 5/5 |

[A]Number of embryos positive per total for classic IBV signs 7 days after inoculation.
*All 6 embryos died 48 hours post-inoculation, presumably from bacterial contamination. Embryos did not show lesions of IBV when examined post-death.

TABLE 3

S1 amino acid sequence comparison of ArkGA vaccine virus passages and viral RNA isolated from vaccinated chickens. Included are amino acid positions in the S1 sequence that exhibited variation among the different ArkGA passages.

| ArkGA Passage | S1 Amino Acid Position | Vaccine Amino Acid | Swab Amino Acid |
|---|---|---|---|
| P1 | 117 | S | S |
|  | 130 | S | S |
|  | 198 | K | K |
|  | 200 | G | G |
|  | 385 | R | R |
| P20 | 117 | S | S |
|  | 130 | S | S |
|  | 198 | K | K/T |
|  | 200 | G | G/D |
|  | 385 | R | R |
| P40 | 117 | S | S |
|  | 130 | S | S/N |
|  | 198 | K | K/T |
|  | 200 | G | G/D |
|  | 385 | R | R |
| P60 | 117 | N | S |
|  | 130 | S | S |
|  | 198 | K | T |
|  | 200 | G | D |
|  | 385 | H | R |

TABLE 4

Ark99 pathogenic virus strain SNPs.

| Protein | CDS Position | Change | Codon Change | Ref. Frequency | Var. Frequency |
|---|---|---|---|---|---|
| Polyprotein 1a | 2,216 | C → T | CCT → CTT | 94.9% | 5.10% |
| Polyprotein 1a | 7,964 | A → T | TAC → TTC | 66.10% | 33.90% |
| Polyprotein 1a | 9,875 | T → C | ATG → ACG | 93.50% | 6.50% |
| Polyprotein 1a | 11,141 | A → G | AAT → AGT | 90.70% | 9.30% |
| Polyprotein 1ab | 12,542 | T → C | TTA → TCA | 94.90% | 5.10% |
| Polyprotein 1ab | 12,968 | C → T | ACG → ATG | 94.90% | 5.10% |
| Polyprotein 1ab | 15,152 | C → A | ACT → AAT | 88.50% | 11.50% |
| Polyprotein 1ab | 16,573 | A → T | AAT → TAT | 92.20% | 7.80% |
| Polyprotein 1ab | 17,517 | G → A | ATG → ATA | 94.00% | 6.00% |
| Spike | 116 | G → A | GGT → GAT | 91.40% | 8.60% |
| Spike | 409 | G → C | GCT → CCT | 94.20% | 5.80% |
| Spike | 815 | C → T | ACT → ATT | 89.20% | 10.80% |
| Spike | 965 | A → T | TAT → TTT | 94.60% | 5.40% |
| Spike | 2,296 | T → C | TTT → CTT | 90.10% | 9.90% |
| Membrane | 26 | C → T | TCG → TTG | 93.40% | 6.60% |
| Membrane | 28 | G → A | GAG → AAG | 91.60% | 8.40% |

TABLE 5

ArkGA P1 (Ark99 vaccine) SNPs.

| Protein | CDS Position | Change | Codon Change | Ref. Frequency | Var. Frequency |
|---|---|---|---|---|---|
| Polyprotein 1a | 52 | C → T | CTC → TTC | 62.60% | 37.40% |
| Polyprotein 1a | 277 | G → T | GGT → TGT | 60.40% | 39.60% |
| Polyprotein 1a | 286 | C → T | CCT → TCT | 92.50% | 7.50% |
| Polyprotein 1a | 1,207 | C → T | CAC → TAC | 93.40% | 6.60% |
| Polyprotein 1a | 2,807 | G → T | TGC → TTC | 88.50% | 11.40% |
| Polyprotein 1a | 8,422 | A → G | ATC → GTC | 70.20% | 29.80% |
| Polyprotein 1a | 8,849 | C → T | GCT → GTT | 62.60% | 37.40% |
| Polyprotein 1a | 10,866 | C → T | ACT → ATT | 85.80% | 14.20% |
| Polyprotein 1ab | 14,444 | C → T | TCA → TTA | 89.10% | 10.90% |
| Polyprotein 1ab | 17,822 | A → G | AAA → AGA | 67.20% | 32.80% |
| Polyprotein 1ab | 19,644 | C → A | CAC → CAA | 88.90% | 11.10% |
| Polyprotein 1ab | 19,757 | A → C | AAA → ACA | 91.50% | 8.50% |
| Spike | 982 | A → G | ATG → GTG | 92.90% | 7.10% |
| Spike | 1,038 | T → G | TTT → TTG | 47.80% | 52.20% |
| Spike | 1,153 | C → T | CGT → TGT | 87.70% | 12.30% |
| Spike | 1,763 | G → A | GGA → GAA | 90.90% | 9.10% |
| Spike | 1,886 | A → T | AAG → ATG | 80.20% | 15.40% |
| Spike | 1,885 | A → C | AAG → CAG | 91.70% | 8.30% |
| Spike | 2,285 | T → C | GTT → GCT | 53.30% | 46.70% |
| Envelope | 308 | A → G | GRA → GGA | 51.20% | 48.80% |
| Membrane | 7 | A → G | RAT → GAT | 51.20% | 48.80% |
| Nucleocapsid | 617 | A → G | GAT → GGT | 59.70% | 40.30% |

TABLE 6

ArkGA P20 SNPs.

| Protein | CDS Position | Change | Codon Change | Ref. Frequency | Var. Frequency |
|---|---|---|---|---|---|
| Polyprotein 1a | 1,106 | A → C | GAG → GCG | 52.90% | 47.10% |
| Polyprotein 1a | 2,202 | G → T | TTG → TTT | 94.90% | 5.10% |
| Polyprotein 1a | 5,300 | G → T | CGT → CTT | 92.30% | 7.70% |
| Polyprotein 1a | 7,701 | G → T | TTG → TTT | 53.30% | 46.70% |
| Polyprotein 1a | 10,342 | C → T | CTT → TTT | 91.90% | 8.10% |
| Polyprotein 1a | 10,816 | G → A | GTT → ATT | 94.90% | 5.10% |
| Polyprotein 1a | 11,686 | G → A | GTC → ATC | 88.00% | 12.00% |
| Polyprotein 1ab | 15,308 | C → T | CCA → CTA | 94.90% | 5.10% |
| Polyprotein 1ab | 17,035 | C → T | CAT → TAT | 91.90% | 8.10% |
| Polyprotein 1ab | 19,542 | G → A | ATG → ATA | 93.70% | 6.30% |
| Spike | 1,709 | C → T | CCT → CTT | 72.10% | 27.90% |
| Spike | 2,563 | G → A | GTG → ATG | 71.50% | 28.50% |
| Nucleocapsid | 289 | G → C | GGA → CGA | 83.10% | 16.90% |
| Nucleocapsid | 806 | C → T | ACA → ATA | 77.60% | 22.40% |
| Nucleocapsid | 916 | G → A | GTC → ATC | 77.20% | 22.80% |
| Nucleocapsid | 922 | C → T | CGT → TGT | 76.70% | 23.30% |
| Nucleocapsid | 1,218 | G → C | GAG → GAC | 94.80% | 5.20% |

TABLE 7

ArkGA P40 SNPs.

| Protein | CDS Position | Change | Codon Change | Ref. Frequency | Var. Frequency |
|---|---|---|---|---|---|
| Polyprotein 1a | 1,106 | C → A | GCG → GAG | 94.80% | 5.20% |
| Polyprotein 1a | 6,527 | A → T | GAT → GCT | 71.40% | 27.70% |
| Polyprotein 1a | 10,393 | C → T | CCC → TCC | 56.00% | 44.00% |
| Polyprotein 1ab | 19,114 | C → T | CCT → TTT | 62.90% | 37.10% |
| Polyprotein 1ab | 19,757 | A → C | AAA → ACA | 67.80% | 32.20% |
| Spike | 350 | G → A | AGC → AAC | 79.70% | 20.30% |
| Spike | 389 | G → A | AGC → AAC | 55.00% | 45.00% |
| Spike | 593 | A → C | AAA → ACA | 72.80% | 27.20% |
| Spike | 599 | G → A | GGT → GAT | 72.00% | 28.00% |
| Spike | 1,154 | G → A | CGT → CAT | 67.40% | 32.60% |
| Spike | 1,709 | C → T | CCT → CTT | 52.90% | 47.10% |
| Spike | 1,750 | T → C | TTT → CTT | 61.00% | 39.00% |
| Spike | 2,563 | G → A | GTG → ATG | 56.50% | 43.30% |
| Spike | 3,032 | C → T | TCT → TTT | 68.40% | 31.60% |
| Spike | 3,107 | A → G | GAT → GGT | 88.50% | 11.50% |
| Spike | 3,112 | G → A | GAG → AAG | 83.60% | 16.40% |
| Nucleocapsid | 289 | G → C | GGA → CGA | 59.00% | 41.00% |
| Nucleocapsid | 787 | A → G | AAT → GTT | 91.50% | 8.50% |
| Nucleocapsid | 806 | C → T | ACA → ATA | 83.20% | 16.80% |
| Nucleocapsid | 916 | G → A | GTC → ATC | 84.90% | 15.10% |
| Nucleocapsid | 922 | C → T | CGT → TGT | 84.80% | 15.20% |
| Nucleocapsid | 1,120 | G → T | GAT → TAT | 92.50% | 7.50% |
| Nucleocapsid | 1,202 | A → G | GAT → GGT | 86.80% | 13.20% |
| Nucleocapsid | 1,218 | G → C | GAG → GAC | 74.10% | 25.70% |
| Membrane | 517 | C → A | CCG → ACG | 81.40% | 18.60% |
| Membrane | 539 | G → A | CGT → CAT | 80.40% | 19.60% |

TABLE 8

ArkGA P60 SNPs.

| Protein | CDS Position | Change | Codon Change | Ref. Frequency | Var. Frequency |
|---|---|---|---|---|---|
| Polyprotein 1a | 293 | C → T | GCA → GTA | 92.00% | 7.60% |
| Polyprotein 1a | 2,807 | G → T | TGC → TTC | 88.00% | 12.00% |
| Polyprotein 1a | 3,029 | A → G | AAA → AGA | 93.90% | 6.00% |
| Polyprotein 1a | 4,204 | T → G | TTT → GTT | 79.70% | 20.30% |
| Polyprotein 1a | 4,712 | A → C | GAA → GCA | 92.80% | 7.20% |
| Polyprotein 1a | 6,527 | C → A | GCT → GAT | 62.80% | 36.80% |
| Polyprotein 1a | 7,701 | G → T | TTG → TTT | 94.30% | 5.70% |
| Polyprotein 1a | 8,141 | A → C | GAC → GCC | 90.80% | 8.70% |
| Polyprotein 1a | 10,393 | C → T | CCC → TCC | 94.00% | 6.00% |
| Polyprotein 1ab | 12,131 | G → T | CGG → CTG | 93.60% | 6.40% |
| Polyprotein 1ab | 13,471 | A → G | ATC → GTC | 93.10% | 6.60% |
| Polyprotein 1ab | 14,014 | G → A | GAA → AAA | 91.50% | 7.90% |
| Polyprotein 1ab | 15,856 | A → G | ACA → GCA | 89.40% | 8.70% |
| Polyprotein 1ab | 18,704 | A → G | AAT → AGT | 94.60% | 5.20% |
| Polyprotein 1ab | 19,114 | T → C | TTT → CTT | 81.40% | 18.60% |
| Polyprotein 1ab | 19,118 | C → T | GCG → GTG | 92.70% | 7.10% |
| Polyprotein 1ab | 19,757 | C → A | ACA → AAA | 76.00% | 24.00% |
| Spike | 158 | C → T | TCT → TTT | 91.30% | 8.30% |
| Spike | 350 | A → G | AAC → AGC | 81.00% | 18.70% |
| Spike | 510 | T → G | AAT → AAG | 93.40% | 6.50% |
| Spike | 593 | A → C | AAA → ACA | 90.40% | 9.60% |
| Spike | 599 | G → A | GGT → GAT | 89.50% | 10.20% |
| Spike | 1,010 | G → A | AGT → AAT | 93.10% | 6.70% |
| Spike | 1,154 | A → G | CAT → CGT | 74.60% | 25.30% |
| Spike | 1,757 | T → A | GTT → GAT | 92.80% | 7.10% |
| Spike | 2,563 | A → G | ATG → GTG | 87.80% | 12.00% |
| Spike | 3,032 | C → T | TCT → TTT | 92.60% | 7.20% |
| Spike | 3,107 | A → G | GAT → GGT | 90.00% | 9.60% |
| Spike | 3,112 | A → G | AAG → GAG | 81.00% | 19.00% |
| Spike | 2,166 | T → C | TTT → CTT | 94.60% | 5.20% |
| Membrane | 539 | A → G | CAT → CGT | 79.70% | 20.00% |
| 5a | 178 | C → A | CCC → ACC | 94.00% | 5.30% |
| 5b | 55 | G → A | GTT → ATT | 78.40% | 21.60% |
| Nucleocapsid | 289 | C → G | CGA → GGA | 81.20% | 18.30% |
| Nucleocapsid | 1,218 | G → C | GAG → GAC | 81.10% | 18.10% |

Discussion

When comparing the ArkGA vaccine candidate to the current ArkDPI vaccine, many differences are observed. Comparison of the S1 portion of the spike protein gene between ArkGA and ArkDPI shows that the two viruses, while serotypically related, are genetically distinct and distinguishable. Comparing the pathogenic version of each virus to the attenuated viruses shows that the ArkGA spike gene appears to be more stable following embryonated egg passage (2 versus 24 amino acid changes). Furthermore, when comparing both ArkGA and ArkDPI vaccines to the pathogenic ArkDPI virus (presumably the virus circulating in the field), we find that the ArkGA virus S1 gene portion is genetically more related. All of this data indicates that the ArkGA vaccine candidate is a better genetic match to pathogenic Ark viruses than the ArkDPI vaccine virus.

When evaluating the whole genomes of the ArkGA passages and comparing them to the Ark99 and ArkDPI pathogenic field strains and the ArkDPI vaccine, the same trend is seen as with comparison of S1. Throughout passaging, the ArkGA vaccine candidates remained highly similar to the Ark99 pathogenic field virus, whereas they are highly different from both the ArkDPI vaccine and field virus. Over the further attenuation process of the ArkGA vaccine candidate, SNPs accumulated over time that may have reduced the pathogenicity of the virus. In particular, the changes seen in the leader sequence and within the spike protein may have contributed to attenuation of the virus, as these regions are associated with viral replication, pathogenicity, and tropism (Ammayappan et al., 2009, *Arch Virol;* 154:495-499, Phillips et al., 2012, *Virus Genes;* 44:63-74, and Zhao et al., 2014, *Intervirology;* 57:319-330). Furthermore, during passaging the frequency of variation was reduced, indicating that the major population within the vaccine virus became more stable over time.

Different passages of the ArkGA vaccine were evaluated for infection, replication, vaccine reaction, and efficacy in broiler chicks. Experimental vaccine and challenge trials showed that the ArkGA P1 vaccine had suitable infection, replication, and induced adequate protection from challenge but was too pathogenic, causing a severe vaccine reaction in the majority of chicks. Further passages in embryonated eggs reduced the severity of the vaccine reaction to 30% for P20, 10% for P40, and 3% for P60. This further attenuation did not adversely affect infection or replication characteristics of the vaccine, as the relative viral load in chicks did not change throughout the trials. ArkGA P60 vaccine coverage was slightly less than expected early post-vaccination, but reached 100% by day 14. This may be attributed to the S1 amino acid changes seen between the vaccine and swab sequences in P60, as the S1 sequences re-isolated from chickens had reverted to the more pathogenic P1 sequence. In the ArkGA P1 vaccine trial a higher vaccine coverage was seen, indicating that these amino acid positions may have an impact on rate of infection. This could be improved by giving a higher dose of the vaccine.

Infection and replication patterns in all trials were predictable and "typical" of what would be expected of an IBV vaccine. This stands in contrast to the infection and replication cycles of the ArkDPI vaccine, which shows very low infection rates and multiple replication cycles during the life of the bird following spray vaccination (Reed and Muench, 1938, *American Journal of Hygiene* 27:493-497). The ArkGA vaccine at P1 and P60 was effective at protecting chickens from a pathogenic Ark IBV challenge. Clinical signs and viral loads post-challenge were significantly lower than non-vaccinated and challenged groups, and all vaccinated birds passed the ciliostasis test. Again, this stands in contrast to previous ArkDPI vaccine and challenge experiments that showed that chickens were clearly not protected from challenge after ArkDPI vaccination by spray (Reed and Muench, 1938, *American Journal of Hygiene* 27:493-497).

The attenuated ArkGA vaccine described herein is a significant improvement over the current commercially available ArkDPI vaccine when comparing infection and replication following spray application and induction of protective immunity following homologous challenge. The ArkGA (P60) is also genetically distinct, making it possible to distinguish the ArkGA vaccine from the ArkDPI vaccine or pathogenic viruses. Further molecular investigation is needed to fully evaluate the 2 amino acid changes seen in the S1 gene in passage 40 and 60, but these changes do not seem to impact the effectiveness of the vaccine. In conclusion, the ArkGA vaccine developed herein is safe when given to 1-day old broilers by spray, and it induces an efficacious immune response against homologous challenge.

Example 2

Molecular Characterization of IBV ArkGA P50 and P60 Isolates

As detailed in Example 1, the S1 subunit of the spike genes for both the P50 ArkGA IBV isolate and the P60 ArkGA IBV isolate were sequenced. The following full-length S1 glycoprotein (IBV S1) nucleic acid sequence was obtained for both the P50 and P60 ArkGA IBV isolates. This nucleotide sequence is also shown in FIG. 9A.

```
                                        (SEQ ID NO: 1)
ATGTTGGTGAAGTCACTGTTTCTAGTGACCATTTTGTTTGCACTATGTA

GTGCTAATTTATATGACAACGAATCTTTTGTGTATTACTACCAGAGTGC

TTTTAGGCCAGGACATGGTTGGCATTTACATGGAGGTGCTTATGCAGTA

GTTAATGTGTCTAGTGAAAATAATAATGCAGGTACTGCCCCAAGTTGCA

CTGCTGGTGCTATTGGCTACAGTAAGAATTTCAGTGCGGCCTCAGTAGC

CATGACTGCACCACTAAGTGGTATGTCATGGTCTGCCTCATCTTTTTGT

ACAGCTCACTGTAATTTTACTTCTTATATAGTGTTTGTTACACATTGTT

TTAAGAACGGATCTAATAGTTGTCCTTTGACAGGTCTTATTCCAAGCGG

TTATATTCGTATTGCTGCTATGAAACATGGAAGTGCTACGCCTGGTCAC

TTATTTTATAACTTAACAGTTTCTGTGACTAAATATCCTAAGTTTAGAT

CGCTACAATGTGTTAATAATCATACTTCTGTATATTTAAATGGTGACCT

TGTTTTCACATCTAACTATACTGAAGATGTTGTAGCTGCAGGTGTCCAT

TTTAAAAGTGGTGGACCTATAACTTATAAAGTTATGAGAGAGGTTAAAG

CCTTGGCTTATTTTGTCAATGGTACTGCACATGATGTCATTCTATGTGA

TGACACACCTAGAGGTTTGTTAGCATGCCAATATAATACTGGCAATTTT

TCAGATGGCTTCTATCCTTTTACTAATACTAGTATTGTTAAGGATAAGT

TTATTGTTTATCGTGAAAGTAGTGTCAATACTACTTTGACATTAACTAA

TTTCACGTTTAGTAATGAAAGTGGTGCCCCTCCTAATACAGGTGGTGTT

GACAGTTTTATTTTATACCAGACACAAACAGCTCAGAGTGGTTATTATA

ATTTTAATTTTTCATTTCTGAGTAGTTTTGTTTATAGGGAAAGTAATTA
```

```
TATGTATGGATCTTACCATCCACGTTGTAGTTTTAGACCTGAAACCCTT

AATGGTTTGTGGTTTAATTCCCTTTCTGTTTCATTAACATACGGTCCCA

TTCAAGGTGGTTGTAAGCAATCTGTATTTAATGGTAAAGCAACTTGTTG

TTATGCTTATTCATACGGAGGACCTCATGCTTGTAAAGGTGTCTATAGA

GGTGAGCTAACACAGCATTTTGAATGTGGTTTGTTAGTTTATGTTACTA

AGAGCGATGGCTCCCGTATACAAACTGCAACACAACCACCTGTATTAAC

CCAAAATTTTTATAATAACATCACTTTAGGTAAGTGTGTTGATTATAAT

GTTTATGGTAGAACTGGACAAGGTTTTATTACTAATGTAACTGATTTAG

CTACTTCTCATAATTACTTAGCGGATGGAGGATTAGCTATTTTAGATAC

ATCTGGTGCCATAGACATCTTCGTTGTACAAGGTGAATATGGCCCTAAC

TACTATAAGGTTAATCTATGTGAAGATGTTAACCAACAGTTTGTAGTTT

CTGGTGGTAAATTAGTAGGTATTCTCACTTCACGTAATGAAACTGGTTC

TCAGCCTCTTGAAAACCAGTTTTACATTAAGATCACTAATGGAACACAT

CGTTCTAGACGTTC
```

The following full length S1 glycoprotein (IBV S1) amino acid sequence was deduced from the nucleotide sequence shown above for the S1 subunit for both the P50 ArkGA IBV and the P60 ArkGA IBV isolates. This sequence is also shown in FIG. 9B.

(SEQ ID NO: 2)
```
MLVKSLFLVTILFALCSANLYDNESFVYYYQSAFRPGHGWHLHGGAYAVV

NVSSENNNAGTAPSCTAGAIGYSKNFSAASVAMTAPLSGMSWSASSFCTA

HCNFTSYIVFVTHCFKNGSNSCPLTGLIPSGYIRIAAMKHGSATPGHLFY

NLTVSVTKYPKFRSLQCVNNHTSVYLNGDLVFTSNYTEDVVAAGVHFKSG

GPITYKVMREVKALAYFVNGTAHDVILCDDTPRGLLACQYNTGNFSDGFY

PFTNTSIVKDKFIVYRESSVNTTLTLTNFTFSNESGAPPNTGGVDSFILY

QTQTAQSGYYNFNFSFLSSFVYRESNYMYGSYHPRCSFRPETLNGLWFNS

LSVSLTYGPIQGGCKQSVFNGKATCCYAYSYGGPHACKGVYRGELTQHFE

CGLLVYVTKSDGSRIQTATQPPVLTQNFYNNITLGKCVDYNVYGRTGQGF

ITNVTDLATSHNYLADGGLAILDTSGAIDIFVVQGEYGPNYYKVNLCEDV

NQQFVVSGGKLVGILTSRNETGSQPLENQFYIKITNGTHRSRR
```

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

SEQUENCE LISTING FREE TEXT

SEQ ID NO: 1 Nucleotide sequence of the S1 subunit of the spike gene for both the P50 ArkGA and P60 ArkGA IBV isolates.

SEQ ID NO: 2 Deduced amino acid sequence of the S1 subunit for both the P50 ArkGA and P60 ArkGA IBV isolates.

SEQ ID NOs: 3-5 Artificial oligonucleotide primer sequences

What is claimed is:

1. An infectious bronchitis virus (IBV) isolate, wherein the IBV isolate comprises the IBV isolate ArkGA p40 deposited at the ATCC under Patent Designation PTA-126834.

2. The IBV isolate of claim 1, wherein the IBV isolate is lyophilized or frozen.

3. A composition comprising the IBV isolate of claim 1.

4. The composition of claim 3 further comprising a pharmaceutically acceptable carrier.

5. The composition of claim 3, wherein the composition is formulated for mucosal administration.

6. The composition of claim 3, wherein the composition is formulated for intranasal, intraocular, or oral administration.

7. The composition of claim 3, wherein the composition is formulated for spraying or aerosolizing.

8. The composition of claim 3, wherein the composition further comprises other viral material.

9. An immunogenic composition comprising the isolated IBV isolate of claim 1.

10. A method of producing an immune response to an infectious bronchitis virus (IBV) in poultry, the method comprising administering the IBV isolate of claim 1.

11. The method of claim 10, wherein the poultry comprises a bird of the order Galliformes.

12. The method of claim 10, wherein the poultry comprises chicken or turkey.

13. The method of claim 10, wherein the IBV isolate is administered by spraying.

14. A method of reducing clinical signs and/or viral load induced by an infectious bronchitis virus (IBV) infection in poultry, the method comprising administering an effective amount of the IBV isolate of claim 1.

15. The method of claim 14, wherein the IBV infection comprises the Arkansas serotype of IBV.

16. A method of reducing susceptibility to disease induced by IBV in poultry, the method comprising administering an effective amount of the IBV isolate of claim 1.

* * * * *